(12) United States Patent
Sheppard et al.

(10) Patent No.: US 7,691,610 B2
(45) Date of Patent: *Apr. 6, 2010

(54) HUMAN ZVEN POLYNUCLEOTIDES

(75) Inventors: Paul O. Sheppard, Granite Falls, WA (US); Paul D. Bishop, Fall City, WA (US)

(73) Assignee: Zymogenetics, Inc., Seattle, WA (US)

( * ) Notice: Subject to any disclaimer, the term of this patent is extended or adjusted under 35 U.S.C. 154(b) by 145 days.

This patent is subject to a terminal disclaimer.

(21) Appl. No.: 11/549,222

(22) Filed: Oct. 13, 2006

(65) Prior Publication Data

US 2007/0048840 A1 Mar. 1, 2007

Related U.S. Application Data

(60) Continuation of application No. 10/982,168, filed on Nov. 5, 2004, now Pat. No. 7,122,349, which is a continuation of application No. 10/212,355, filed on Aug. 2, 2002, now Pat. No. 6,828,425, which is a division of application No. 09/712,529, filed on Nov. 14, 2000, now Pat. No. 6,485,938.

(60) Provisional application No. 60/165,905, filed on Nov. 16, 1999, provisional application No. 60/184,875, filed on Feb. 25, 2000, provisional application No. 60/197,750, filed on Apr. 19, 2000, provisional application No. 60/210,332, filed on Jun. 7, 2000.

(51) Int. Cl.
C12P 21/02 (2006.01)
C12N 1/21 (2006.01)
C12N 1/18 (2006.01)
C07H 21/02 (2006.01)
C12N 5/04 (2006.01)
C12N 5/06 (2006.01)

(52) U.S. Cl. .................. 435/69.5; 435/320.1; 435/325; 435/252.3; 435/254.2; 435/419; 435/348; 435/349; 536/23.1

(58) Field of Classification Search ....................... None
See application file for complete search history.

(56) References Cited

U.S. PATENT DOCUMENTS

| | | | |
|---|---|---|---|
| 5,294,630 A | 3/1994 | Blake et al. | |
| 5,891,720 A | 4/1999 | Moore et al. | |
| 6,042,821 A | 3/2000 | DeMarsh et al. | |
| 6,284,725 B1 | 9/2001 | Coolidge et al. | |
| 6,485,938 B1 * | 11/2002 | Sheppard et al. | 435/69.1 |
| 6,756,479 B2 | 6/2004 | Sheppard et al. | |
| 6,828,425 B2 | 12/2004 | Sheppard et al. | |
| 7,045,299 B2 | 5/2006 | Ohtaki et al. | |
| 7,052,674 B2 | 5/2006 | Zhou et al. | |
| 7,122,349 B2 * | 10/2006 | Sheppard et al. | 435/69.1 |
| 7,179,787 B2 | 2/2007 | Sheppard et al. | |
| 7,205,110 B2 | 4/2007 | Thompson et al. | |
| 7,264,801 B2 * | 9/2007 | Ferrara et al. | 424/130.1 |
| 7,291,589 B2 | 11/2007 | Thompson et al. | |
| 7,531,311 B2 | 5/2009 | Thompson et al. | |
| 2002/0115610 A1 | 8/2002 | Zhou et al. | |
| 2002/0172678 A1 * | 11/2002 | Ferrara et al. | 424/145.1 |
| 2002/0187523 A1 | 12/2002 | Tang et al. | |
| 2002/0188330 A1 | 12/2002 | Gielen et al. | |
| 2002/0192634 A1 | 12/2002 | Ferrara et al. | |
| 2007/0042417 A1 | 2/2007 | Sheppard et al. | |
| 2007/0042960 A1 | 2/2007 | Sheppard et al. | |
| 2007/0048258 A1 | 3/2007 | Thompson et al. | |
| 2007/0048778 A1 | 3/2007 | Thompson et al. | |
| 2007/0048805 A1 | 3/2007 | Sheppard et al. | |
| 2007/0049526 A1 | 3/2007 | Thompson et al. | |
| 2007/0053907 A1 | 3/2007 | Thompson et al. | |
| 2007/0053908 A1 | 3/2007 | Thompson et al. | |
| 2007/0065403 A1 | 3/2007 | Thompson et al. | |
| 2007/0065404 A1 | 3/2007 | Thompson et al. | |
| 2007/0065405 A1 | 3/2007 | Thompson et al. | |
| 2007/0078259 A1 | 4/2007 | Thompson et al. | |
| 2007/0087414 A1 | 4/2007 | Thompson et al. | |
| 2007/0092912 A1 | 4/2007 | Thompson et al. | |
| 2007/0172889 A1 | 7/2007 | Sheppard et al. | |
| 2008/0219985 A1 | 9/2008 | Thompson et al. | |

FOREIGN PATENT DOCUMENTS

| | | |
|---|---|---|
| EP | 1357129 | 10/2003 |
| EP | 1506971 | 2/2005 |
| EP | 1589033 | 10/2005 |
| EP | 1688434 | 8/2006 |

(Continued)

OTHER PUBLICATIONS

Bassil et al., "Prokineticin-2, motilin, ghrelin and metoclopramide: Prokinetic utility in mouse stomach and colon", European Journal of Pharmacology 524:138-144, 2005.
Boisbouvier et al., "A Structural Homologue of Colipase in Black Mamba Venom Revealed by NMR Floating Disulphide Bridge Analysis," J. Mol. Biol. 283: 205-219, 1998.
EMBL Accession No. AF182066, Dec. 14, 1999.
EMBL Accession No. AF182069, Oct. 2, 2000.
EMBL Accession No. AF333024, May 5, 2001.
EMBL Accession No. AF333025, May 5, 2001.
Fedi et al., "Isolation and Biochemical Characterization of the Human Dkk-1 Homologue, a Novel Inhibitor of Mammalian Wnt Signaling," J.Biol. Chem. 274(27): 19465-19472, 1999.

(Continued)

*Primary Examiner*—Cherie M Woodward
(74) *Attorney, Agent, or Firm*—Knobbe Martens Olson & Bear LLP

(57) ABSTRACT

The present invention provides a new family of human proteins, designated as "Zven," as agents that stimulate gastrointestinal contractility, gastric emptying, intestinal transit, and treating gastroparesis. The Zven1 gene, which resides in human chromosome 3p21.1-3p14.3, is expressed in testicular tissue and peripheral blood lymphocytes. The invention also provides methods for using the antibodies to detect the presence of the protein with antibodies and methods for using the polynucleotides to detect the presence of Zven RNA.

11 Claims, No Drawings

FOREIGN PATENT DOCUMENTS

| WO | WO 99/06550 | 2/1999 |
| --- | --- | --- |
| WO | WO 99/63088 | 12/1999 |
| WO | WO 01/36465 | 5/2001 |
| WO | WO 01/48015 | 7/2001 |
| WO | WO 02/36625 | 5/2002 |
| WO | WO 02/62944 | 8/2002 |
| WO | WO 03/40326 | 5/2003 |
| WO | WO 2004/031367 | 4/2004 |
| WO | WO 2004/040000 | 5/2004 |
| WO | WO 2004/065419 | 8/2004 |
| WO | WO 2004/081229 | 9/2004 |
| WO | WO 2005/037870 | 4/2005 |

OTHER PUBLICATIONS

Harlow et al., "Antibodies A Laboratory Manual," Cold Spring Harbor Laboratory, pp. 76, 361, 476, 555 and 626, 1988.

Hsieh et al., "A new secreted protein that binds to Wnt proteins and inhibits their activities," Nature 398: 431-436, 1999.

Jilek et al., "Murine *Bv8* Gene Maps Near a Synteny Breakpoint of Mouse Chromosome 6 and Human 3p21," Gene 256: 189-195, 2000.

Joubert et al., "The Amino Acid Sequence of Protein A from dendroaspis polylepis polylepis (Black mamba) Venom," Hoppe Seylers Z Physiol Chem. 361(12): 1787-94, 1980.

Li et al., "Identification of Two Prokineticin cDNAs: Recombinant Proteins Potently Contract Gastrointestinal Smooth Muscle," Molec. Pharmacol. 59(4): 692-698, 2001.

Mollay et al., "Bv8, a small protein from frog skin and its homologue from snake venom induce hyperalgensia in rats," Euro J Pharmacol. 374: 189-196, 1999.

Morrison et al., "Genetically Engineered Antibody Molecules," Advances in Immunology 44: 65-92, 1989.

Panés, J., "Inflammatory Bowel Disease: Pathogenesis and Targets for Therapeutic Interventions," Acta Physiol Scand. 173: 159-165, 2001.

Schweitz et al., "MIT1, a Black Mamba Toxin With a New and Highly Potent Activity on Intestinal Contraction," FEBS Lett. 461: 183-188, 1999.

Wechselberger et al., "The Mammalian Homologues of Frog Bv8 are Mainly Expressed in Spermatocytes," FEBS Lett. 462: 177-181, 1999.

WPI Accession No. 2004-593431, 2004.

WPI Accession No. 2005-322854, 2005.

International Search Report dated Aug. 3, 2001 for Application No. PCT/US00/31278, filed Nov. 14, 2000.

Baumgart et al., "Inflammatory Bowel Disease: Cause and Immunobiology," Lancet 369(9573): 1627-1640, 2007.

Casset et al., "A Peptide Mimetic of an Anti-CD4 Monoclonal Antibody by Rational Design," Biochem Biophys Res Commun. 307: 198-205, 2003.

Colman et al., "Effects of Amino Acid Sequence Changes on Antibody-Antigen Interactions," Res Immuno. 145(1): 33 36, Jan. 1994.

DATABASE UniPrto [Online] "RecName: Full=Prokineticin-2; Short=PK2; Altname: Full=Protein Bv8 homolog; Flags: Precursor." EBI accession No. Uniprot:Q9HC23; Database Accession No. Q9HC23 (Sep. 26, 2001).

Lin et al. "Identification and molecular characterization of two closely related G protein-coupled receptors activated by prokineticins/endocrine gland vascular endothelial growth factor." Journal of Biological Chemistry. 277(22):19276-19280 (2002).

MacCallum et al., "Antibody-Antigen Interactions: Contact Analysis and Binding Site Topography," J Mol Biol 262: 732-745, 1996.

Ngo et al., "Computational Complexity, Protein Structure Prediction, and the Levinthal Paradox," in *The Protein Folding Problem and Tertiary Structure Prediction* by Merz et al., Eds. pp. 491-495, 1994.

Paul, (Ed) "Structure and Function of Immunoglobulins", Fundamental Immunology, 3rd Edition, Raven Press, NY, 1993, pp. 292-295, Chapter 9.

Rudikoff et al., "Single Amino Acid Substitution Altering Antigen-Binding Specificity," PNAS USA 79: 1979-1983, Mar. 1982.

Wells, James A., "Additivity of Mutational Effects in Proteins," Biochemistry 29(37): 8509-8517, 1990.

Xavier et al., "Unravelling the Pathogenesis of Inflammatory Bowel Disease," Nature 448: 427-434, 2007.

European Search Report for European Application No. 03773168.4, dated Jun. 10, 2009.

Supplementary European Search Report for European Application No. 03786525.0, dated Jun. 15, 2009.

\* cited by examiner

HUMAN ZVEN POLYNUCLEOTIDES

CROSS-REFERENCE TO RELATED APPLICATIONS

This application is a continuation of U.S. application Ser. No. 10/982,168, filed Nov. 5, 2004, now U.S. Pat. No. 7,122, 349 which is a continuation of U.S. application Ser. No. 10/212,355, filed Aug. 2, 2002, now U.S. Pat. No. 6,828,425, which is a divisional of U.S. application Ser. No. 09/712,529, filed Nov. 14, 2000, now U.S. Pat. No. 6,485,938, which claims the benefit of U.S. Provisional Application No. 60/165,905, filed Nov. 16, 1999, U.S. Provisional Application No. 60/184,875, filed Feb. 25, 2000, U.S. Provisional Application No. 60/197,750, filed Apr. 19, 2000, and U.S. Provisional Application No. 60/210,332, filed Jun. 7, 2000, all of which are herein incorporated by reference.

TECHNICAL FIELD

The present invention relates generally to new polypeptides having diagnostic and therapeutic uses. In particular, the present invention relates to polypeptides, designated "Zven1" and "Zven2," and to nucleic acid molecules encoding the Zven polypeptides.

BACKGROUND OF THE INVENTION

Cellular differentiation of multicellular organisms is controlled by hormones and polypeptide growth factors. These diffusable molecules allow cells to communicate with each other, to act in concert to form tissues and organs, and to repair and regenerate damaged tissue. Examples of hormones and growth factors include the steroid hormones, parathyroid hormone, follicle stimulating hormone, the interferons, the interleukins, platelet derived growth factor, epidermal growth factor, and granulocyte-macrophage colony stimulating factor, among others.

Hormones and growth factors influence cellular metabolism by binding to receptor proteins. Certain receptors are integral membrane proteins that bind with the hormone or growth factor outside the cell, and that are linked to signaling pathways within the cell, such as second messenger systems. Other classes of receptors are soluble intracellular molecules.

Wnt proteins are emerging as one of the pre-eminent families of signaling molecules in animal development. To date, murine Wnt genes include Wnt-1, Wnt-2, Wnt-2B/13, Wnt-3, Wnt-3A, Wnt-4, Wnt-5A, Wnt-5B, Wnt-6, Wnt-7A, Wnt-7B, Wnt-8A, Wnt-8B, Wnt-10A, Wnt-10B, Wnt-11, and Wnt-15, while the following human Wnt genes have been described: Wnt-1, Wnt-2, Wnt-2B/13, Wnt-3, Wnt-4, Wnt-5A, Wnt-7A, Wnt-8A, Wnt-8B, Wnt-10B, Wnt-11, Wnt-14, and Wnt-15. See, for example, Nusse and Varmus, *Cell* 31:99 (1982), van Ooyen et al., *EMBO J.* 4:2905 (1985), Wainwright et al., *EMBO J.* 7:1743 (1988), McMahon and McMahon, *Development* 107:643 (1989), Gavin et al., *Genes Dev.* 4:2319 (1990), Roelink et al., *Proc. Nat'l Acad. Sci. USA* 87:4519 (1990), Roelink and Nusse, *Genes Dev.* 5:381 (1991), Clark et al., *Genomics* 18:249 (1993), Roelink et al., *Genomics* 17:790 (1993), Adamson et al., *Genomics* 24:9 (1994), Huguet et al., *Cancer Res.* 54:2615 (1994), Bouillet, *Mech. Dev.* 58:141 (1996), Ikegawa et al., *Cytogenet. Cell Genet.* 74:149 (1996), Katoh et al., *Oncogene* 13:873 (1996), Lako et al., *Genomics* 35:386 (1996), Wang and Shackleford, *Oncogene* 13:1537 (1996), Bergstein, *Genomics* 46:450 (1997), Bui et al., *Oncogene* 14:1249 (1997), and Grove et al., *Development* 125:2315 (1998).

Wnt genes typically encode secreted glycoproteins having 350-400 amino acids, and the proteins often include a conserved pattern of 23-24 cysteine residues in addition to other invariant residues (Cadigan and Nusse, *Genes & Dev.* 11:3286 (1997)). Following cellular secretion, Wnt proteins are believed to reside mainly in the extracellular matrix or to associated with the cellular surface.

According to the classical Wnt signaling pathway model, Wnt proteins induce gene expression by de-repressing a signal pathway via a so-called "Frizzled" transmembrane receptor (see, for example, Brown and Moon, *Curr. Opin. Cell Biol.* 10:182 (1998)). In the absence of Wnt, glycogen synthase kinase-3β activity results in the degradation of the free cytosolic pool of β-catenin. The association of cognate Wnt proteins and Frizzled receptors leads to the activation of a signaling pathway. The most proximal intracellular component of this pathway is the Disheveled protein, which becomes phosphorylated and inhibits glycogen synthase kinase-3β. Consequently, the pool of intracellular β-catenin increases, and β-catenin can interact with members of the lymphoid enhancer/T cell factor (LEF/TCF) family of architectural transcription factors in the nucleus. These complexes bind consensus LEF/TCF sites in promoters and induce transcription of Wnt-responsive genes.

The Wnt proteins are multipotent, and the proteins are capable of inducing different biological responses in both embryonic and adult contexts (see, for example, Ingham, *TIG* 12:382 (1996)). This type of broad activity is shared with fibroblast growth factors, transforming growth factors β, and nerve growth factors (Nusse and Varmus, *Cell* 69:1073 (1992)). When over-expressed, Wnt proteins can promote tumor formation (Erdreich-Epstein and Shackleford, *Growth Factors* 15:149 (1998)). Knock-out mutations in mice have shown Wnt proteins to be essential for brain development, and the out growth of embryonic primordia for kidney, tail bud and limb bud (McMahon and Bradley, *Cell* 62:1073 (1990), Thomas and Capecchi, *Nature* 346:847 (1990), Stark et al., *Nature* 372:679 (1994), Takada et al., *Genes Dev.* 8:174 (1994), and Parr and McMahon, *Nature* 374:350 (1995)).

Several secreted factors inhibit Wnt signaling (see, for example, Finch et al., *Proc. Nat'l Acad. Sci. USA* 94:6770 (1997); Moon et al., *Cell* 88:725 (1997); Luyten et al., WO 98/16641); Brown and Moon, *Curr. Opin. Cell Biol.* 10:182 (1998); Aikawa et al., *J. Cell. Sci.* 112:3815 (1999)). The Frzb proteins, for example, bind to secreted Wnt proteins and prevent productive interactions between Wnt and Frizzled proteins. These proteins contain a region that is homologous to a putative Wnt-binding domain of Frizzled proteins. Wnt-inhibitory factor-1 is another type of secreted protein, which binds to Wnt proteins and inhibits Wnt signaling (Hsieh et al., *Nature* 398:431 (1999)). Wnt-inhibitory factor-1 proteins are produced by fish, amphibia, and mammals, indicating the importance of these inhibitory proteins (Hsieh et al., *Nature* 398:431 (1999)).

Inhibitors of Wnt signaling can be used to block the inducement of tumor formation by inappropriate Wnt expression. Accordingly, a need exists for the provision of new Wnt inhibitory proteins.

BRIEF SUMMARY OF THE INVENTION

The present invention provides members of a new human gene family, designated as "Zven," and, in particular, illustrative members of the gene family, designated "Zven1" and "Zven2." The present invention also provides Zven1 and Zven2 polypeptides and fusion proteins, nucleic acid molecules encoding such polypeptides and proteins, and methods for using these nucleotide and amino acid sequences.

DESCRIPTION OF THE INVENTION

1. Overview

The present invention provides nucleic acid molecules that encode human Zven polypeptides. An illustrative nucleic acid molecule containing a sequence that encodes the Zven1 polypeptide has the nucleotide sequence of SEQ ID NO:1. The encoded polypeptide has the following amino acid sequence: MRSLCCAPLL LLLLLPPLLL TPRAGDAAVI TGACDKDSQC GGGMCCAVSI WVKSIRICTP MGKLGDSCHP LTRKVPFFGR RMHHTCPCLP GLACL-RTSFN RFICLAQK (SEQ ID NO:2). Thus, the Zven1 nucleotide sequence described herein encodes a polypeptide of 108 amino acids. The putative signal sequences of Zven1 polypeptide reside at amino acid residues 1 to 20, 1 to 21, and 1 to 22 of SEQ ID NO:2.

Zven1 is expressed in eosinophils, and northern analysis indicates Zven1 gene expression is present in human testicular tissue and peripheral blood lymphocytes. As described in Example 1, Zven1 is expressed in B cell, T cell, monocyte, and granulocyte cell lines. Moreover, Zven1 gene expression was detectable in unactivated monocytes, but not in activated monocytes. Thus, Zven1 gene expression can be used to differentiate between unactivated and activated monocytes. Example 2 describes studies, which indicate that Zven1 can inhibit the proliferation of lung tumor cells. The Zven1 gene resides in human chromosome 3p21.1-3p14.3.

An illustrative nucleic acid molecule containing a sequence that encodes the Zven2 polypeptide has the nucleotide sequence of SEQ ID NO:4. The encoded polypeptide has the following amino acid sequence: MRGATRVSIM LLLVTVSDCA VITGACERDV QCGAGTCCAI SLWLR-GLRMC TPLGREGEEC HPGSHKVPFF RKRKHHTCPC LPNLLCSRFP DGRYRCSMDL KNINF (SEQ ID NO:5). Thus, the Zven2 nucleotide sequence described herein encodes a polypeptide of 105 amino acids. The putative signal sequences of Zven2 polypeptide reside at amino acid residues 1 to 17, and 1 to 19 of SEQ ID NO:5.

Northern analyses show that the Zven2 gene is highly expressed in human testicular and ovarian tissue. High levels of Zven2 gene expression were also detected in placenta, adrenal gland, and prostate. In contrast, little or no Zven2 gene expression was evident in heart, brain, lung, small intestine, liver, skeletal muscle, kidney, pancreas, spleen, thymus, colon, peripheral blood lymphocytes, stomach, thyroid, spinal cord, lymph node, trachea, and bone marrow. Accordingly, Zven2 nucleic acid probes and anti-Zven2 antibodies can be used to differentiate between various tissues.

Sequence analysis revealed a homology relationship between Zven2 and dkk-1, a potent inhibitor of Wnt action reported in amphibians and humans (Glinka et al., *Nature* 391:357 (1998); Fedi et al., *J. Biol. Chem.* 274:19465 (1999)). Since the activation of Wnt signaling can contribute to the neoplastic process, a Wnt inhibitor can provide a useful therapeutic protein.

As described below, the present invention provides isolated polypeptides comprising an amino acid sequence that is at least 70%, at least 75%, at least 80%, at least 85%, at least 90%, or at least 95% identical to amino acid residues 23 to 108 of SEQ ID NO:2. Certain of such isolated polypeptides can specifically bind with an antibody that specifically binds with a polypeptide consisting of the amino acid sequence of SEQ ID NO:2. Particular polypeptides can inhibit the proliferation of lung tumor cells. An illustrative polypeptide is a polypeptide that comprises the amino acid sequence of SEQ ID NO:2.

Similarly, the present invention includes provides isolated polypeptides comprising an amino acid sequence that is at least 70%, at least 75%, at least 80%, at least 85%, at least 90%, or at least 95% identical to amino acid residues 20 to 105 of SEQ ID NO:5, wherein such isolated polypeptides can specifically bind with an antibody that specifically binds with a polypeptide consisting of the amino acid sequence of SEQ ID NO:5. An illustrative polypeptide is a polypeptide that comprises the amino acid sequence of SEQ ID NO:5.

The present invention also provides polypeptides comprising an amino acid sequence selected from the group consisting of: (1) amino acid residues 21 to 108 of SEQ ID NO:2, (2) amino acid residues 22 to 108 of SEQ ID NO:2, (3) amino acid residues 23 to 108 of SEQ ID NO:2, (4) amino acid residues 82 to 108 of SEQ ID NO:2, (5) amino acid residues 1 to 78 (amide) of SEQ ID NO:2, (6) amino acid residues 1 to 79 of SEQ ID NO:2, (7) amino acid residues 21 to 78 (amide) of SEQ ID NO:2, (8) amino acid residues 21 to 79 of SEQ ID NO:2, (9) amino acid residues 22 to 78 (amide) of SEQ ID NO:2, (10) amino acid residues 22 to 79 of SEQ ID NO:2, (II) amino acid residues 23 to 78 (amide) of SEQ ID NO:2, (12) amino acid residues 23 to 79 of SEQ ID NO:2, (13) amino acid residues 20 to 108 of SEQ ID NO:2, (14) amino acid residues 20 to 72 of SEQ ID NO:2, (15) amino acid residues 20 to 79 of SEQ ID NO:2, (16) amino acid residues 20 to 79 (amide) of SEQ ID NO:2, (17) amino acid residues 21 to 72 of SEQ ID NO:2, (18) amino acid residues 21 to 79 (amide) of SEQ ID NO:2, (19) amino acid residues 22 to 72 of SEQ ID NO:2, (20) amino acid residues 22 to 79 (amide) of SEQ ID NO:2, (21) amino acid residues 23 to 72 of SEQ ID NO:2, (22) amino acid residues 23 to 79 (amide) of SEQ ID NO:2, (23) amino acid residues 28 to 108 of SEQ ID NO:2, (24) amino acid residues 28 to 72 of SEQ ID NO:2, (25) amino acid residues 28 to 79 of SEQ ID NO:2, (26) amino acid residues 28 to 79 (amide) of SEQ ID NO:2, (27) amino acid residues 75 to 108 of SEQ ID NO:2, (28) amino acid residues 75 to 79 of SEQ ID NO:2, and (29) amino acid residues 75 to 78 (amide) of SEQ ID NO:2. Illustrative polypeptides consist of amino acid sequences (1) to (29).

The present invention further includes polypeptides comprising an amino acid sequence selected from the group consisting of: (a) amino acid residues 20 to 105 of SEQ ID NO:5, (b) amino acid residues 18 to 105 of SEQ ID NO:5, (c) amino acid residues 1 to 70 of SEQ ID NO:5, (d) amino acid residues 20 to 70 of SEQ ID NO:5, (e) amino acid residues 18 to 70 of SEQ ID NO:5, (f) amino acid residues 76 to 105 of SEQ ID NO:5, (g) amino acid residues 66 to 105 of SEQ ID NO:5, and (h) amino acid residues 82 to 105 of SEQ ID NO:5. Illustrative polypeptides consist of amino acid sequences (a) to (h).

The present invention further provides antibodies and antibody fragments that specifically bind with such polypeptides. Exemplary antibodies include polyclonal antibodies, murine monoclonal antibodies, humanized antibodies derived from murine monoclonal antibodies, and human monoclonal antibodies. Illustrative antibody fragments include F(ab')$_2$, F(ab)$_2$, Fab', Fab, Fv, scFv, and minimal recognition units. The present invention also includes anti-idiotype antibodies that specifically bind with such antibodies or antibody fragments. The present invention further includes compositions comprising a carrier and a peptide, polypeptide, antibody, or anti-idiotype antibody described herein.

The present invention also provides isolated nucleic acid molecules that encode a Zven polypeptide, wherein the nucleic acid molecule is selected from the group consisting of (a) a nucleic acid molecule comprising the nucleotide sequence of SEQ ID NO:3, (b) a nucleic acid molecule encoding the amino acid sequence of SEQ ID NO:2, (c) a nucleic acid molecule that remains hybridized following stringent wash conditions to a nucleic acid molecule consisting of the nucleotide sequence of nucleotides 66 to 161 of SEQ ID NO:1, the nucleotide sequence of nucleotides 288 to 389 of SEQ ID NO:1, or to the complement of the nucleotide sequence of either nucleotides 66 to 161 of SEQ ID NO:1 or nucleotides 288 to 389 of SEQ ID NO:1, (d) a nucleic acid molecule comprising the nucleotide sequence of SEQ ID NO:6, (e) a nucleic acid molecule encoding the amino acid sequence of SEQ ID NO:5, (f) a nucleic acid molecule that remains hybridized following stringent wash conditions to a nucleic acid molecule consisting of the nucleotide sequence of nucleotides 334 to 405 of SEQ ID NO:4, or to the complement of the nucleotide sequence of nucleotides 334 to 405 of SEQ ID NO:4.

Illustrative nucleic acid molecules include those in which any difference between the amino acid sequence encoded by the nucleic acid molecule and the corresponding amino acid sequence of either SEQ ID NO:2 or SEQ ID NO:5 is due to a conservative amino acid substitution. The present invention further contemplates isolated nucleic acid molecules that comprise a nucleotide sequence of nucleotides 132 to 389 of SEQ ID NO:1, and nucleotides 148 to 405 of SEQ ID NO:4.

The present invention also includes vectors and expression vectors comprising such nucleic acid molecules. Such expression vectors may comprise a transcription promoter, and a transcription terminator, wherein the promoter is operably linked with the nucleic acid molecule, and wherein the nucleic acid molecule is operably linked with the transcription terminator. The present invention further includes recombinant host cells comprising these vectors and expression vectors. Illustrative host cells include bacterial, yeast, avian, fungal, insect, mammalian, and plant cells. Recombinant host cells comprising such expression vectors can be used to prepare Zven polypeptides by culturing such recombinant host cells that comprise the expression vector and that produce the Zven protein, and, optionally, isolating the Zven protein from the cultured recombinant host cells. The present invention further includes products made by such processes.

In addition, the present invention provides pharmaceutical compositions comprising a pharmaceutically acceptable carrier and at least one of such an expression vector or recombinant virus comprising such expression vectors.

The present invention also contemplates methods for detecting the presence of Zven1 RNA in a biological sample, comprising the steps of (a) contacting a Zven1 nucleic acid probe under hybridizing conditions with either (i) test RNA molecules isolated from the biological sample, or (ii) nucleic acid molecules synthesized from the isolated RNA molecules, wherein the probe has a nucleotide sequence comprising a portion of the nucleotide sequence of SEQ ID NO:1, or its complement, and (b) detecting the formation of hybrids of the nucleic acid probe and either the test RNA molecules or the synthesized nucleic acid molecules, wherein the presence of the hybrids indicates the presence of Zven1 RNA in the biological sample. Analogous methods can be used to detect the presence of Zven2 RNA in a biological sample, wherein the probe has a nucleotide sequence comprising a portion of the nucleotide sequence of SEQ ID NO:4, or its complement.

The present invention further provides methods for detecting the presence of Zven polypeptide in a biological sample, comprising the steps of: (a) contacting the biological sample with an antibody or an antibody fragment that specifically binds with a polypeptide either consisting of the amino acid sequence of SEQ ID NO:2 or consisting of the amino acid sequence of SEQ ID NO:5, wherein the contacting is performed under conditions that allow the binding of the antibody or antibody fragment to the biological sample, and (b) detecting any of the bound antibody or bound antibody fragment. Such an antibody or antibody fragment may further comprise a detectable label selected from the group consisting of radioisotope, fluorescent label, chemiluminescent label, enzyme label, bioluminescent label, and colloidal gold.

Illustrative biological samples include human tissue, such as an autopsy sample, a biopsy sample, and the like.

The present invention also provides kits for performing these detection methods. For example, a kit for detection of Zven1 gene expression may comprise a container that comprises a nucleic acid molecule, wherein the nucleic acid molecule is selected from the group consisting of (a) a nucleic acid molecule comprising the nucleotide sequence of nucleotides 66 to 161 of SEQ ID NO:1, (b) a nucleic acid molecule comprising the nucleotide sequence of nucleotides 288 to 389 of SEQ ID NO:1, (c) a nucleic acid molecule comprising the complement of the nucleotide sequence of nucleic acid molecules (a) or (b), (d) a nucleic acid molecule that is a fragment of (a) consisting of at least eight nucleotides, (e) a nucleic acid molecule that is a fragment of (b) consisting of at least eight nucleotides, and (f) a nucleic acid molecule that is a fragment of (c) consisting of at least eight nucleotides. A kit for detection of Zven2 gene expression may comprise a container that comprises a nucleic acid molecule, wherein the nucleic acid molecule is selected from the group consisting of (a) a nucleic acid molecule comprising the nucleotide sequence of nucleotides 334 to 405 of SEQ ID NO:4, (b) a nucleic acid molecule comprising the complement of the nucleotide sequence of (a), (c) a nucleic acid molecule that is a fragment of (a) consisting of at least eight nucleotides, and (d) a nucleic acid molecule that is a fragment of (b) consisting of at least eight nucleotides. Such kits may also comprise a second container that comprises one or more reagents capable of indicating the presence of the nucleic acid molecule.

On the other hand, a kit for detection of Zven protein may comprise a container that comprises an antibody, or an antibody fragment, that specifically binds with a polypeptide consisting of the amino acid sequence of SEQ ID NO:2 or consisting of the amino acid sequence of SEQ ID NO:5.

The present invention also contemplates anti-idiotype antibodies, or anti-idiotype antibody fragments, that specifically bind an antibody or antibody fragment that specifically binds a polypeptide consisting of the amino acid sequence of SEQ ID NO:2 or the amino acid sequence of SEQ ID NO:5.

The present invention further provides variant Zven1 polypeptides, which comprise an amino acid sequence that shares an identity with the amino acid sequence of SEQ ID NO:2 selected from the group consisting of at least 70% identity, at least 80% identity, at least 90% identity, at least 95% identity, or greater than 95% identity, and wherein any difference between the amino acid sequence of the variant polypeptide and the amino acid sequence of SEQ ID NO:2 is due to one or more conservative amino acid substitutions. Illustrative variant Zven2 polypeptides, which comprise an amino acid sequence that shares an identity with the amino acid sequence of SEQ ID NO:5 selected from the group consisting of at least 70% identity, at least 80% identity, at least 90% identity, at least 95% identity, or greater than 95% identity, and wherein any difference between the amino acid sequence of the variant polypeptide and the amino acid sequence of SEQ ID NO:5 is due to one or more conservative amino acid substitutions.

The present invention also provides fusion proteins comprising a Zven1 polypeptide moiety or a Zven2 polypeptide moiety. Such fusion proteins can further comprise an immunoglobulin moiety. A suitable immunoglobulin moiety is an immunoglobulin heavy chain constant region, such as a human $F_C$ fragment. The present invention also includes isolated nucleic acid molecules that encode such fusion proteins.

The present invention also includes methods of inhibiting the proliferation of tumor cells (e.g., lung tumor cells), comprising the step of administering a composition comprising Zven1 to the tumor cells. In an in vivo approach, the composition is a pharmaceutical composition, administered in a therapeutically effective amount to a subject, which has a tumor. Such in vivo administration can provide at least one physiological effect selected from the group consisting of decreased number of tumor cells, decreased metastasis, decreased size of a solid tumor, and increased necrosis of a tumor.

These and other aspects of the invention will become evident upon reference to the following detailed description. In addition, various references are identified below and are incorporated by reference in their entirety.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et a., *J. Biol. Chem.* 269:25728 (1994)), SPI, cAMP response element binding protein (CREB; Loeken, *Gene Expr.* 3:253 (1993)) and octamer factors (see, in general, Watson et al., eds., *Molecular Biology of the Gene*, 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces a Zven1 or Zven2 peptide or polypeptide from an expression vector. In contrast, such polypeptides can be produced by a cell that is a "natural source" of Zven1 or Zven2, and that lacks an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of a Zven1 or Zven2 polypeptide fused with a polypeptide that binds an affinity matrix. Such a fusion protein provides a means to isolate large quantities of Zven1 or Zven2 using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ M$^{-1}$.

An "anti-idiotype antibody" is an antibody that binds with the variable region domain of an immunoglobulin. In the present context, an anti-idiotype antibody binds with the variable region of an anti-Zven1 or anti-Zven2 antibody, and thus, an anti-idiotype antibody mimics an epitope of Zven1 or Zven2.

An "antibody fragment" is a portion of an antibody such as F(ab')$_2$, F(ab)$_2$, Fab', Fab, and the like. Regardless of structure, an antibody fragment binds with the same antigen that is recognized by the intact antibody. For example, an anti-Zven1 monoclonal antibody fragment binds with an epitope of Zven1.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNAs encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide, which will bind a major histocompatibility complex molecule to form an MHC-peptide complex which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell which binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "antisense gene." Anti-sense RNA molecules are capable of binding to mRNA molecules, resulting in an inhibition of mRNA translation.

An "anti-sense oligonucleotide specific for Zven1" or a "Zven1 anti-sense oligonucleotide" is an oligonucleotide having a sequence (a) capable of forming a stable triplex with a portion of the Zven1 gene, or (b) capable of forming a stable duplex with a portion of an mRNA transcript of the Zven1 gene. Similarly, an "anti-sense oligonucleotide specific for Zven2" or a "Zven2 anti-sense oligonucleotide" is an oligonucleotide having a sequence (a) capable of forming a stable triplex with a portion of the Zven2 gene, or (b) capable of forming a stable duplex with a portion of an mRNA transcript of the Zven2 gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "variant Zven1 gene" refers to nucleic acid molecules that encode a polypeptide having an amino acid sequence that is a modification of SEQ ID NO:2. Such variants include naturally-occurring polymorphisms of Zven1 genes, as well as synthetic genes that contain conservative amino acid substitutions of the amino acid sequence of SEQ ID NO:2. Additional variant forms of Zven1 genes are nucleic acid molecules that contain insertions or deletions of the nucleotide sequences described herein. A variant Zven1 gene can be identified by determining whether the gene hybridizes with a nucleic acid molecule having the nucleotide sequence of SEQ ID NO:1, or its complement, under stringent conditions. Similarly, a variant Zven2 gene and a variant Zven2 polypeptide can be identified with reference to SEQ ID NO:4 and SEQ ID NO:5, respectively.

Alternatively, variant Zven genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in *Methods in Gene Biotechnology*, pages 123-151 (CRC Press, Inc. 1997), and Bishop (ed.), *Guide to Human Genome Computing*, 2nd Edition (Academic Press, Inc. 1998)). Particular methods for determining sequence identity are described below.

Regardless of the particular method used to identify a variant Zven1 gene or variant Zven1 polypeptide, a variant gene or polypeptide encoded by a variant gene may be characterized by its ability to bind specifically to an anti-Zven1 antibody. Similarly, a variant Zven2 gene product or variant Zven2 polypeptide may be characterized by its ability to bind specifically to an anti-Zven2 antibody.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

The present invention includes functional fragments of Zven1 and Zven2 genes. Within the context of this invention, a "functional fragment" of a Zven1 (or Zven2) gene refers to a nucleic acid molecule that encodes a portion of a Zven1 (or Zven2) polypeptide, which specifically binds with an anti-Zven1 (anti-Zven2) antibody.

Due to the imprecision of standard analytical methods, molecular weights and lengths of polymers are understood to be approximate values. When such a value is expressed as "about" X or "approximately" X, the stated value of X will be understood to be accurate to ±10%.

3. Production of Human Zven1 and Zven2 Genes

Nucleic acid molecules encoding a human Zven1 gene can be obtained by screening a human cDNA or genomic library using polynucleotide probes based upon SEQ ID NO:1. Similarly, nucleic acid molecules encoding a human Zven2 gene can be obtained by screening a human cDNA or genomic library using polynucleotide probes based upon SEQ ID NO:4. These techniques are standard and well-established.

As an illustration, a nucleic acid molecule that encodes a human Zven1 gene can be isolated from a human cDNA library. In this case, the first step would be to prepare the cDNA library by isolating RNA from tissues, such as testis or peripheral blood lymphocytes, using methods well-known to those of skill in the art. In general, RNA isolation techniques must provide a method for breaking cells, a means of inhibiting RNase-directed degradation of RNA, and a method of separating RNA from DNA, protein, and polysaccharide contaminants. For example, total RNA can be isolated by freezing tissue in liquid nitrogen, grinding the frozen tissue with a mortar and pestle to lyse the cells, extracting the ground tissue with a solution of phenol/chloroform to remove proteins, and separating RNA from the remaining impurities by selective precipitation with lithium chloride (see, for example, Ausubel et al. (eds.), *Short Protocols in Molecular Biology*, $3^{rd}$ Edition, pages 4-1 to 4-6 (John Wiley & Sons 1995) ["Ausubel (1995)"]; Wu et al., *Methods in Gene Biotechnology*, pages 33-41 (CRC Press, Inc. 1997) ["Wu (1997)"]). Alternatively, total RNA can be isolated from tissue by extracting ground tissue with guanidinium isothiocyanate, extracting with organic solvents, and separating RNA from contaminants using differential centrifugation (see, for example, Chirgwin et al., *Biochemistry* 18:52 (1979); Ausubel (1995) at pages 4-1 to 4-6; Wu (1997) at pages 33-41).

In order to construct a cDNA library, poly(A) RNA must be isolated from a total RNA preparation. Poly(A)$^+$ RNA can be isolated from total RNA using the standard technique of oligo (dT)-cellulose chromatography (see, for example, Aviv and Leder, *Proc. Nat'l Acad. Sci. USA* 69:1408 (1972); Ausubel (1995) at pages 4-11 to 4-12).

Double-stranded cDNA molecules are synthesized from poly(A)$^+$ RNA using techniques well-known to those in the art. (see, for example, Wu (1997) at pages 41-46). Moreover, commercially available kits can be used to synthesize double-stranded cDNA molecules. For example, such kits are available from Life Technologies, Inc. (Gaithersburg, Md.), CLONTECH Laboratories, Inc. (Palo Alto, Calif.), Promega Corporation (Madison, Wis.) and STRATAGENE (La Jolla, Calif.).

Various cloning vectors are appropriate for the construction of a cDNA library. For example, a cDNA library can be prepared in a vector derived from bacteriophage, such as a λgt10 vector. See, for example, Huynh et al., "Constructing and Screening cDNA Libraries in λgt10 and λ gt11," in *DNA Cloning: A Practical Approach* Vol. 1, Glover (ed.), page 49 (IRL Press, 1985); Wu (1997) at pages 47-52.

Alternatively, double-stranded cDNA molecules can be inserted into a plasmid vector, such as a PBLUESCRIPT vector (STRATAGENE; La Jolla, Calif.), a LAMDAGEM-4 (Promega Corp.) or other commercially available vectors. Suitable cloning vectors also can be obtained from the American Type Culture Collection (Manassas, Va.)

To amplify the cloned cDNA molecules, the cDNA library is inserted into a prokaryotic host, using standard techniques. For example, a cDNA library can be introduced into competent *E. coli* DH5 cells, which can be obtained, for example, from Life Technologies, Inc. (Gaithersburg, Md.).

A human genomic library can be prepared by means well-known in the art (see, for example, Ausubel (1995) at pages 5-1 to 5-6; Wu (1997) at pages 307-327). Genomic DNA can be isolated by lysing tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient.

DNA fragments that are suitable for the production of a genomic library can be obtained by the random shearing of genomic DNA or by the partial digestion of genomic DNA with restriction endonucleases. Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are well-known in the art (see, for example, Ausubel (1995) at pages 5-1 to 5-6; Wu (1997) at pages 307-327).

Nucleic acid molecules that encode a human Zven1 or Zven2 gene can also be obtained using the polymerase chain reaction (PCR) with oligonucleotide primers having nucleotide sequences that are based upon the nucleotide sequences described herein. General methods for screening libraries with PCR are provided by, for example, Yu et al., "Use of the Polymerase Chain Reaction to Screen Phage Libraries," in *Methods in Molecular Biology*, Vol. 15: *PCR Protocols: Current Methods and Applications*, White (ed.), pages 211-215 (Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology*, Vol. 15: *PCR Protocols: Current Methods and Applications*, White (ed.), pages 317-337 (Humana Press, Inc. 1993).

Alternatively, human genomic libraries can be obtained from commercial sources such as Research Genetics (Huntsville, Ala.) and the American Type Culture Collection (Manassas, Va.).

A library containing cDNA or genomic clones can be screened with one or more polynucleotide probes based upon SEQ ID NO:1, using standard methods (see, for example, Ausubel (1995) at pages 6-1 to 6-11).

Anti-Zven antibodies, produced as described below, can also be used to isolate DNA sequences that encode human Zven genes from cDNA libraries. For example, the antibodies can be used to screen λgt11 expression libraries, or the antibodies can be used for immunoscreening following hybrid selection and translation (see, for example, Ausubel (1995) at pages 6-12 to 6-16; Margolis et al., "Screening λ expression libraries with antibody and protein probes," in *DNA Cloning 2: Expression Systems,* 2nd Edition, Glover et al. (eds.), pages 1-14 (Oxford University Press 1995)).

As an alternative, a Zven gene can be obtained by synthesizing nucleic acid molecules using mutually priming long oligonucleotides and the nucleotide sequences described herein (see, for example, Ausubel (1995) at pages 8-8 to 8-9). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology*, Vol. 15: *PCR Protocols: Current Methods and Applications*, White (ed.), pages 263-268, (Humana Press, Inc. 1993), and Holowachuk et al., *PCR Methods Appl.* 4:299 (1995)).

The nucleic acid molecules of the present invention can also be synthesized with "gene machines" using protocols such as the phosphoramidite method. If chemically-synthesized double stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes (>300 base pairs), however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. For reviews on polynucleotide synthesis, see, for example, Glick and Pasternak, *Molecular Biotechnology, Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

The sequence of a Zven cDNA or Zven genomic fragment can be determined using standard methods. Zven polynucleotide sequences disclosed herein can also be used as probes or primers to clone 5' non-coding regions of a Zven gene. Promoter elements from a Zven gene can be used to direct the expression of heterologous genes in tissues of, for example, transgenic animals or patients treated with gene therapy. The identification of genomic fragments containing a Zven promoter or regulatory element can be achieved using well-established techniques, such as deletion analysis (see, generally, Ausubel (1995)).

Cloning of 5' flanking sequences also facilitates production of Zven proteins by "gene activation," as disclosed in U.S. Pat. No. 5,641,670. Briefly, expression of an endogenous Zven gene in a cell is altered by introducing into the Zven locus a DNA construct comprising at least a targeting sequence, a regulatory sequence, an exon, and an unpaired splice donor site. The targeting sequence is a Zven 5' non-coding sequence that permits homologous recombination of the construct with the endogenous Zven locus, whereby the sequences within the construct become operably linked with the endogenous Zven coding sequence. In this way, an endogenous Zven promoter can be replaced or supplemented with other regulatory sequences to provide enhanced, tissue-specific, or otherwise regulated expression.

4. Production of Zven Gene Variants

The present invention provides a variety of nucleic acid molecules, including DNA and RNA molecules, which encode the Zven polypeptides disclosed herein. Those skilled in the art will readily recognize that, in view of the degeneracy of the genetic code, considerable sequence variation is possible among these polynucleotide molecules. SEQ ID NOs:3 and 6 are a degenerate nucleotide sequences that encompasses all nucleic acid molecules that encode the Zven polypeptides of SEQ ID NOs:2 and 5, respectively. Those skilled in the art will recognize that the degenerate sequence of SEQ ID NO:3 also provides all RNA sequences encoding SEQ ID NO:2, by substituting U for T, while the degenerate sequence of SEQ ID NO:6 also provides all RNA sequences encoding SEQ ID NO:5, by substituting U for T. Thus, the present invention contemplates Zven1 polypeptide-encoding nucleic acid molecules comprising nucleotide 66 to nucleotide 389 of SEQ ID NO:1, and their RNA equivalents, as well as Zven2 polypeptide-encoding nucleic acid molecules comprising nucleotide 91 to nucleotide 405 of SEQ ID NO:4, and their RNA equivalents.

Table 1 sets forth the one-letter codes used within SEQ ID NOs:3 and 6 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NOs:3 and 6, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B |  | RAY |
| Glu\|Gln | Z |  | SAR |
| Any | X |  | NNN |

One of ordinary skill in the art will appreciate that some ambiguity is introduced in determining a degenerate codon, representative of all possible codons encoding an amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NOs:2 and 5. Variant sequences can be readily tested for functionality as described herein.

Different species can exhibit "preferential codon usage." In general, see, Grantham et al., *Nuc. Acids Res.* 8:1893 (1980), Haas et al. *Curr. Biol.* 6:315 (1996), Wain-Hobson et al., *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opin. Genet. Dev.* 4:851 (1994), Kane, *Curr. Opin. Biotechnol.* 6:494 (1995), and Makrides, *Microbiol. Rev.* 60:512 (1996). As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACCC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed in SEQ ID NOs:3 and 6 serve as templates for optimizing expression of polynucleotides in various cell types and species commonly used in the art and disclosed herein. Sequences containing preferential codons can be tested and optimized for expression in various species, and tested for functionality as disclosed herein.

The present invention further provides variant polypeptides and nucleic acid molecules that represent counterparts from other species (orthologs). These species include, but are not limited to mammalian, avian, amphibian, reptile, fish, insect and other vertebrate and invertebrate species. Of particular interest are Zven polypeptides from other mammalian species, including porcine, ovine, bovine, canine, feline, equine, and other primate polypeptides. Orthologs of human Zven can be cloned using information and compositions provided by the present invention in combination with conventional cloning techniques. For example, a cDNA can be cloned using mRNA obtained from a tissue or cell type that expresses Zven. Suitable sources of mRNA can be identified by probing northern blots with probes designed from the sequences disclosed herein. A library is then prepared from mRNA of a positive tissue or cell line.

A Zven-encoding cDNA molecule can then be isolated by a variety of methods, such as by probing with a complete or partial human cDNA or with one or more sets of degenerate probes based on the disclosed sequences. A cDNA can also be cloned using the polymerase chain reaction with primers designed from the representative human Zven sequences disclosed herein. Within an additional method, the cDNA library can be used to transform or transfect host cells, and expression of the cDNA of interest can be detected with an antibody to Zven polypeptide. Similar techniques can also be applied to the isolation of genomic clones.

Those skilled in the art will recognize that the sequences disclosed in SEQ ID NOs:1 and 4 represent single alleles of human Zven1 and Zven2, respectively, and that allelic variation and alternative splicing are expected to occur. Allelic variants of this sequence can be cloned by probing cDNA or genomic libraries from different individuals according to standard procedures. Allelic variants of the nucleotide sequences shown in SEQ ID NOs:1 and 4, including those containing silent mutations and those in which mutations result in amino acid sequence changes, are within the scope of the present invention, as are proteins which are allelic variants of SEQ ID NOs:2 and 5. cDNA molecules generated from alternatively spliced mRNAs, which retain the properties of the Zven polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Within certain embodiments of the invention, the isolated nucleic acid molecules can hybridize under stringent conditions to nucleic acid molecules comprising nucleotide sequences disclosed herein. For example, such nucleic acid molecules can hybridize under stringent conditions to nucleic acid molecules consisting of the nucleotide sequence of SEQ ID NO:1, to nucleic acid molecules consisting of the nucleotide sequence of nucleotides 66 to 161 of SEQ ID NO:1, to nucleic acid molecules consisting of the nucleotide sequence of nucleotides 288 to 389 of SEQ ID NO:1, to nucleic acid molecules consisting of the nucleotide sequence of SEQ ID NO:4, to nucleic acid molecules consisting of the nucleotide sequence of nucleotides 334 to 405 of SEQ ID NO:4, or to nucleic acid molecules consisting of nucleotide sequences that are the complements of such sequences. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$ of the mismatched hybrid decreases by 1° C. for every 1-1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Stringent hybridization conditions encompass temperatures of about 5-25° C. below the $T_m$ of the hybrid and a hybridization buffer having up to 1 M $Na^+$. Higher degrees of stringency at lower temperatures can be achieved with the addition of formamide which reduces the $T_m$ of the hybrid about 1° C. for each 1% formamide in the buffer solution. Generally, such stringent conditions include temperatures of 20-70° C. and a hybridization buffer containing up to 6×SSC and 0-50% formamide. A higher degree of stringency can be achieved at temperatures of from 40-70° C. with a hybridization buffer having up to 4×SSC and from 0-50% formamide. Highly stringent conditions typically encompass temperatures of 42-70° C. with a hybridization buffer having up to 1×SSC and 0-50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polypeptide hybrid. The $T_m$ for a specific target sequence is the temperature (under defined conditions) at which 50% of the target sequence will hybridize to a perfectly matched probe sequence. Those conditions that influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.),

*Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and Primer Premier 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20-25° C. below the calculated $T_m$. For smaller probes, <50 base pairs, hybridization is typically carried out at the $T_m$ or 5-10° C. below. This allows for the maximum rate of hybridization for DNA-DNA and DNA-RNA hybrids.

The length of the polynucleotide sequence influences the rate and stability of hybrid formation. Smaller probe sequences, <50 base pairs, reach equilibrium with complementary sequences rapidly, but may form less stable hybrids. Incubation times of anywhere from minutes to hours can be used to achieve hybrid formation. Longer probe sequences come to equilibrium more slowly, but form more stable complexes even at lower temperatures. Incubations are allowed to proceed overnight or longer. Generally, incubations are carried out for a period equal to three times the calculated Cot time. Cot time, the time it takes for the polynucleotide sequences to reassociate, can be calculated for a particular sequence by methods known in the art.

The base pair composition of polynucleotide sequence will effect the thermal stability of the hybrid complex, thereby influencing the choice of hybridization temperature and the ionic strength of the hybridization buffer. A-T pairs are less stable than G-C pairs in aqueous solutions containing sodium chloride. Therefore, the higher the G-C content, the more stable the hybrid. Even distribution of G and C residues within the sequence also contribute positively to hybrid stability. In addition, the base pair composition can be manipulated to alter the $T_m$ of a given sequence. For example, 5-methyldeoxycytidine can be substituted for deoxycytidine and 5-bromodeoxyuridine can be substituted for thymidine to increase the $T_m$, whereas 7-deazz-2'-deoxyguanosine can be substituted for guanosine to reduce dependence on $T_m$.

The ionic concentration of the hybridization buffer also affects the stability of the hybrid. Hybridization buffers generally contain blocking agents such as Denhardt's solution (Sigma Chemical Co., St. Louis, Mo.), denatured salmon sperm DNA, tRNA, milk powders (BLOTTO), heparin or SDS, and a $Na^+$ source, such as SSC (1×SSC: 0.15 M sodium chloride, 15 mM sodium citrate) or SSPE (1×SSPE: 1.8 M NaCl, 10 mM $NaH_2PO_4$, 1 mM EDTA, pH 7.7). By decreasing the ionic concentration of the buffer, the stability of the hybrid is increased. Typically, hybridization buffers contain from between 10 mM-1 M $Na^+$. The addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

As an illustration, a nucleic acid molecule encoding a variant Zven1 polypeptide can be hybridized with a nucleic acid molecule having the nucleotide sequence of SEQ ID NO:1 (or its complement) at 42° C. overnight in a solution comprising 50% formamide, 5×SSC (1×SSC: 0.15 M sodium chloride and 15 mM sodium citrate), 50 mM sodium phosphate (pH 7.6), 5× Denhardt's solution (100× Denhardt's solution: 2% (w/v) Ficoll 400, 2% (w/v) polyvinylpyrrolidone, and 2% (w/v) bovine serum albumin), 10% dextran sulfate, and 20 μg/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g., EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×-2×SSC with 0.1% sodium dodecyl sulfate (SDS) at 55-65° C. For example, nucleic acid molecules encoding particular variant Zven1 polypeptides can remain hybridized with a nucleic acid molecule consisting of the nucleotide sequence of nucleotides 66 to 161 of SEQ ID NO:1, the nucleotide sequence of nucleotides 288 to 389 of SEQ ID NO:1, or their complements, following washing under stringent washing conditions, in which the wash stringency is equivalent to 0.5×-2×SSC with 0.1% SDS at 55-65° C., including 0.5×SSC with 0.1% SDS at 55° C., or 2×SSC with 0.1% SDS at 65° C. In a similar manner, nucleic acid molecules encoding particular Zven2 variants can remain hybridized with a nucleic acid molecule consisting of the nucleotide sequence of nucleotides 334 to 405 of SEQ ID NO:4, or its complement, following washing under stringent washing conditions, in which the wash stringency is equivalent to 0.5×-2×SSC with 0.1% SDS at 55-65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×-0.2×SSC with 0.1% sodium dodecyl sulfate (SDS) at 50-65° C. As an illustration, nucleic acid molecules encoding particular variant Zven1 polypeptides can remain hybridized with a nucleic acid molecule consisting of the nucleotide sequence of nucleotides 66 to 161 of SEQ ID NO:1, the nucleotide sequence of nucleotides 288 to 389 of SEQ ID NO:1, or their complements, following washing under highly stringent washing conditions, in which the wash stringency is equivalent to 0.1×-0.2×SSC with 0.1% SDS at 50-65° C., including 0.1×SSC with 0.1% SDS at 50° C., or 0.2×SSC with 0.1% SDS at 65° C. Similarly, nucleic acid molecules encoding particular Zven2 variants remain hybridized with a nucleic acid molecule consisting of the nucleotide sequence of nucleotides 334 to 405 of SEQ ID NO:4, or its complement, following washing under highly stringent washing conditions, in which the wash stringency is equivalent to 0.1×-0.2×SSC with 0.1% SDS at 50-65° C., including 0.1×SSC with 0.1% SDS at 50° C., or 0.2×SSC with 0.1% SDS at 65° C.

The present invention also provides isolated Zven1 polypeptides that have a substantially similar sequence identity to the polypeptides of SEQ ID NO:2, or their orthologs. The term "substantially similar sequence identity" is used herein to denote polypeptides having 85%, 90%, 95% or greater than 95% sequence identity to the sequences shown in SEQ ID NO:2, or their orthologs. Similarly, the present invention provides isolated Zven2 polypeptides having 85%, 90%, 95% or greater than 95% sequence identity to the sequences shown in SEQ ID NO:5, or their orthologs.

The present invention also contemplates Zven variant nucleic acid molecules that can be identified using two criteria: a determination of the similarity between the encoded polypeptide with the amino acid sequence of SEQ ID NOs:2 or 5, and a hybridization assay, as described above. For example, certain Zven1 gene variants include nucleic acid molecules (1) that remain hybridized with a nucleic acid molecule consisting of the nucleotide sequence of nucleotides 66 to 161 of SEQ ID NO:1, the nucleotide sequence of nucleotides 288 to 389 of SEQ ID NO:1, or their complements, following washing under stringent washing conditions, in which the wash stringency is equivalent to 0.5×-2× SSC with 0.1% SDS at 55-65° C., and (2) that encode a polypeptide having 85%, 90%, 95% or greater than 95% sequence identity to the amino acid sequence of SEQ ID NO:2. Alternatively, certain Zven1 variant genes can be characterized as nucleic acid molecules (1) that remain hybridized with a nucleic acid molecule consisting of the nucleotide sequence of nucleotides 66 to 161 of SEQ ID NO:1, the nucleotide sequence of nucleotides 288 to 389 of SEQ ID NO:1, or their complements, following washing under highly stringent washing conditions, in which the wash stringency is equivalent to 0.1×-0.2×SSC with 0.1% SDS at 50-65° C., and (2) that encode a polypeptide having 85%, 90%, 95% or greater than 95% sequence identity to the amino acid sequence of SEQ ID NO:2.

Moreover, certain Zven2 gene variants include nucleic acid molecules (1) that remain hybridized with a nucleic acid molecule consisting of the nucleotide sequence of nucleotides 334 to 405 of SEQ ID NO:4, or its complement, following washing under stringent washing conditions, in which the wash stringency is equivalent to 0.5×-2×SSC with 0.1% SDS at 55-65° C., and (2) that encode a polypeptide having 85%, 90%, 95% or greater than 95% sequence identity to the amino acid sequence of SEQ ID NO:5. Alternatively, certain Zven2 variant genes can be characterized as nucleic acid molecules (1) that remain hybridized with a nucleic acid molecule consisting of the nucleotide sequence of nucleotides 334 to 405 of SEQ ID NO:4, or its complement, following washing under highly stringent washing conditions, in which the wash stringency is equivalent to 0.1×-0.2×SSC with 0.1% SDS at 50-65° C., and (2) that encode a polypeptide having 85%, 90%, 95% or greater than 95% sequence identity to the amino acid sequence of SEQ ID NO:5.

Percent sequence identity is determined by conventional methods. See, for example, Altschul et al., *Bull. Math. Bio.* 48:603 (1986), and Henikoff and Henikoff, Proc. Natl. Acad. Sci. USA 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 3 (amino acids are indicated by the standard one-letter codes). The percent identity is then calculated as: ([Total number of identical matches]/[length of the longer sequence plus the number of gaps introduced into the longer sequence in order to align the two sequences])(100).

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative Zven1 or Zven2 variant. The FASTA algorithm is described by Pearson and Lipman, *Proc. Nat'l Acad. Sci. USA* 85:2444 (1988), and by Pearson, Meth. Enzymol. 183:63 (1990).

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, and most preferably, three. The other parameters can be set as: gap opening penalty=10, and gap extension penalty=1.

The present invention includes nucleic acid molecules that encode a polypeptide having a conservative amino acid change, compared with the amino acid sequence of SEQ ID NOs:2 or 5. That is, variants can be obtained that contain one or more amino acid substitutions of SEQ ID NOs:2 or 5, in which an alkyl amino acid is substituted for an alkyl amino acid in a Zven1 or Zven2 amino acid sequence, an aromatic amino acid is substituted for an aromatic amino acid in a Zven1 or Zven2 amino acid sequence, a sulfur-containing amino acid is substituted for a sulfur-containing amino acid in a Zven1 or Zven2 amino acid sequence, a hydroxy-containing amino acid is substituted for a hydroxy-containing amino acid in a Zven1 or Zven2 amino acid sequence, an acidic amino acid is substituted for an acidic amino acid in a Zven1 or Zven2 amino acid sequence, a basic amino acid is substituted for a basic amino acid in a Zven1 or Zven2 amino acid sequence, or a dibasic monocarboxylic amino acid is substituted for a dibasic monocarboxylic amino acid in a Zven1 or Zven2 amino acid sequence.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Particular variants of Zven1 or Zven2 are characterized by having at least 70%, at least 80%, at least 85%, at least 90%, at least 95% or greater than 95% sequence identity to a corresponding amino acid sequence disclosed herein (i.e., SEQ ID NO:2 or SEQ ID NO:5), wherein the variation in amino acid sequence is due to one or more conservative amino acid substitutions.

Conservative amino acid changes in a Zven1 gene and a Zven2 gene can be introduced by substituting nucleotides for the nucleotides recited in SEQ ID NO:1 and SEQ ID NO:4, respectively. Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8-10 to 8-22; and McPherson (ed.), *Directed Mutagenesis: A Practical Approach* (IRL Press 1991)).

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanne, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc. Nat'l Acad. Sci. USA* 90:10145 (1993).

In a second method, translation is carried out in *Xenopus* oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

A limited number of non-conservative amino acids, amino acids that are not encoded by the genetic code, non-naturally occurring amino acids, and unnatural amino acids may be substituted for Zven amino acid residues.

Amino acid sequence analysis indicates that Zven1 and Zven2 share several motifs. For example, one motif is "AVITGAC[DE][KR]D," (SEQ ID NO:8), wherein acceptable amino acids for a given position are indicated within square brackets. This motif occurs in Zven1 at amino acid residues 28 to 37 of SEQ ID NO:2, and in Zven2 at amino acid residues 20 to 29 of SEQ ID NO:5. Another motif is "CHP[GL][ST][HR]KVPFFX[KR]RXHHTCPCLP," (SEQ ID NO:9), wherein acceptable amino acids for a given position are indicated within square brackets, and "X" can be any amino acid residue. This motif occurs in Zven1 at amino acid residues 68 to 90 in SEQ ID NO:2, and in Zven2 at amino acid residues 60 to 82 of SEQ ID NO:5. The present invention includes peptides and polypeptides comprising these motifs.

Sequence analysis also indicated that Zven1 and Zven2 include various conservative amino acid substitutions with respect to each other. Accordingly, particular Zven1 variants can be designed by modifying its sequence to include one or more amino acid substitutions corresponding with the Zven2 sequence, while particular Zven2 variants can be designed by modifying its sequence to include one or more amino acid substitutions corresponding with the Zven1 sequence. Such variants can be constructed using Table 4, which presents exemplary conservative amino acid substitutions found in Zven1 and Zven2. Although Zven1 and Zven2 variants can be designed with any number of amino acid substitutions, certain variants will include at least about X amino acid substitutions wherein X is selected from the group consisting of 2, 5, 7, 10, 12, 14, 16, 18, and 20.

TABLE 4

| Zven1 | | Zven2 | |
|---|---|---|---|
| Amino acid Position (SEQ ID NO: 2) | Amino acid | Amino acid Position (SEQ ID NO: 5) | Amino acid |
| 4 | Leu | 4 | Ala |
| 7 | Ala | 7 | Val |
| 9 | Leu | 9 | Ile |
| 14 | Leu | 14 | Val |
| 35 | Asp | 27 | Glu |
| 36 | Lys | 28 | Arg |
| 42 | Gly | 34 | Ala |
| 48 | Val | 40 | Ile |
| 50 | Ile | 42 | Leu |
| 52 | Val | 44 | Leu |
| 53 | Lys | 45 | Arg |
| 55 | Ile | 47 | Leu |
| 63 | Lys | 55 | Arg |
| 66 | Asp | 58 | Glu |
| 71 | Leu | 63 | Gly |
| 72 | Thr | 64 | Ser |
| 73 | Arg | 65 | His |
| 80 | Arg | 72 | Lys |
| 93 | Ala | 85 | Leu |
| 102 | Phe | 94 | Tyr |

Essential amino acids in the polypeptides of the present invention can be identified procedures known in the art, such as site-directed mutagenesis or alanine-scanning mutagenesis (Cunningham and Wells, *Science* 244:1081 (1989), Bass et al., *Proc. Nat'l Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological activity, such as the ability to bind to an antibody, to identify amino acid residues that are critical to the activity of the molecule. See also, Hilton et al., *J. Biol. Chem.* 271:4699 (1996).

The location of Zven1 or Zven2 receptor binding domains can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306 (1992), Smith et al., *J. Mol. Biol.* 224:899 (1992), and Wlodaver et al., *FEBS Lett.* 309:59 (1992). Moreover, Zven1 or Zven2 labeled with biotin or FITC can be used for expression cloning of Zven1 or Zven2 receptors.

Multiple amino acid substitutions can be made and tested using known methods of mutagenesis and screening, such as those disclosed by Reidhaar-Olson and Sauer (*Science* 241:53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204, and region-directed mutagenesis (Derbyshire et al., *Gene* 46:145 (1986), and Ner et al., *DNA* 7:127, (1988)).

Variants of the disclosed Zven1 or Zven2 nucleotide and polypeptide sequences can also be generated through DNA shuffling as disclosed by Stemmer, *Nature* 370:389 (1994), Stemmer, *Proc. Nat'l Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-Zven1 or anti-Zven2 antibodies, can be recovered from the host cells and rapidly sequenced using modem equipment. These methods allow the rapid determination of the importance of individual amino acid residues in a polypeptide of interest, and can be applied to polypeptides of unknown structure.

The present invention also includes "functional fragments" of Zven1 or Zven2 polypeptides and nucleic acid molecules encoding such functional fragments. Routine deletion analyses of nucleic acid molecules can be performed to obtain functional fragments of a nucleic acid molecule that encodes a Zven1 or Zven2 polypeptide. As an illustration, DNA molecules having the nucleotide sequence of SEQ ID NO:1 can be digested with Bal31 nuclease to obtain a series of nested deletions. The fragments are then inserted into expression vectors in proper reading frame, and the expressed polypeptides are isolated and tested for the ability to bind anti-Zven antibodies. One alternative to exonuclease digestion is to use oligonucleotide-directed mutagenesis to introduce deletions or stop codons to specify production of a desired fragment. Alternatively, particular fragments of a Zven gene can be synthesized using the polymerase chain reaction.

Methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2-5A synthetase induced by human interferon," in *Biological*

*Interferon Systems, Proceedings of ISIR-TNO Meeting on Interferon Systems*, Cantell (ed.), pages 65-72 (Nijhoff 1987), Herschman, "The EGF Receptor," in *Control of Animal Cell Proliferation*, Vol. 1, Boynton et al., (eds.) pages 169-199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of a Zven1 or Zven2 gene that have amino acid changes, compared with the amino acid sequence of SEQ ID NO:2 or SEQ ID NO:5. A variant Zven gene can be identified on the basis of structure by determining the level of identity with the particular nucleotide and amino acid sequences disclosed herein. An alternative approach to identifying a variant gene on the basis of structure is to determine whether a nucleic acid molecule encoding a potential variant Zven1 or Zven2 gene can hybridize to a nucleic acid molecule having the nucleotide sequence of SEQ ID NO:1 or SEQ ID NO:4, as discussed above.

The present invention also provides polypeptide fragments or peptides comprising an epitope-bearing portion of a Zven1 or Zven2 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides can contain at least four to ten amino acids, at least ten to fifteen amino acids, or about 15 to about 30 amino acids of SEQ ID NOs:2 or 5. Such epitope-bearing peptides and polypeptides can be produced by fragmenting a Zven1 or Zven2 polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105-116 (The Humana Press, Inc. 1992), Price, "Production and Characterization of Synthetic Peptide-Derived Antibodies," in *Monoclonal Antibodies: Production, Engineering, and Clinical Application*, Ritter and Ladyman (eds.), pages 60-84 (Cambridge University Press 1995), and Coligan et al. (eds.), *Current Protocols in Immunology*, pages 9.3.1-9.3.5 and pages 9.4.1-9.4.11 (John Wiley & Sons 1997).

Regardless of the particular nucleotide sequence of a variant Zven1 or Zven2 gene, the gene encodes a polypeptide that may be characterized by its ability to bind specifically to an anti-Zven1 or anti-Zven2 antibody.

In addition to the uses described above, polynucleotides and polypeptides of the present invention are useful as educational tools in laboratory practicum kits for courses related to genetics and molecular biology, protein chemistry, and antibody production and analysis. Due to its unique polynucleotide and polypeptide sequences, molecules of Zven1 or Zven2 can be used as standards or as "unknowns" for testing purposes. For example, Zven1 or Zven2 polynucleotides can be used as an aid, such as, for example, to teach a student how to prepare expression constructs for bacterial, viral, or mammalian expression, including fusion constructs, wherein Zven1 or Zven2 is the gene to be expressed; for determining the restriction endonuclease cleavage sites of the polynucleotides; determining mRNA and DNA localization of Zven1 or Zven2 polynucleotides in tissues (i.e., by northern and Southern blotting as well as polymerase chain reaction); and for identifying related polynucleotides and polypeptides by nucleic acid hybridization. As an illustration, students will find that PvuII digestion of a nucleic acid molecule consisting of the nucleotide sequence of nucleotides 66 to 389 of SEQ ID NO:1 provides two fragments of about 123 base pairs, and 201 base pairs, whereas HaeIII digestion yields fragments of about 46 base pairs, and 278 base pairs.

Zven1 or Zven2 polypeptides can be used as an aid to teach preparation of antibodies; identifying proteins by western blotting; protein purification; determining the weight of expressed Zven1 or Zven2 polypeptides as a ratio to total protein expressed; identifying peptide cleavage sites; coupling amino and carboxyl terminal tags; amino acid sequence analysis, as well as, but not limited to monitoring biological activities of both the native and tagged protein (i.e., protease inhibition) in vitro and in vivo. For example, students will find that digestion of unglycosylated Zven1 with cyanogen bromide yields four fragments having approximate molecular weights of 148, 4337, 1909, 2402, and 2939, whereas digestion of unglycosylated Zven1 with BNPS or NCS/urea yields fragments having approximate molecular weights of 5231, and 6444.

Zven1 or Zven2 polypeptides can also be used to teach analytical skills such as mass spectrometry, circular dichroism, to determine conformation, especially of the four alpha helices, x-ray crystallography to determine the three-dimensional structure in atomic detail, nuclear magnetic resonance spectroscopy to reveal the structure of proteins in solution. For example, a kit containing Zven1 or Zven2 can be given to the student to analyze. Since the amino acid sequence would be known by the instructor, the protein can be given to the student as a test to determine the skills or develop the skills of the student, the instructor would then know whether or not the student has correctly analyzed the polypeptide. Since every polypeptide is unique, the educational utility of Zven1 or Zven2 would be unique unto itself.

The antibodies which bind specifically to Zven1 or Zven2 can be used as a teaching aid to instruct students how to prepare affinity chromatography columns to purify Zven1 or Zven2, cloning and sequencing the polynucleotide that encodes an antibody and thus as a practicum for teaching a student how to design humanized antibodies. The Zven1 or Zven2 gene, polypeptide, or antibody would then be packaged by reagent companies and sold to educational institutions so that the students gain skill in art of molecular biology. Because each gene and protein is unique, each gene and protein creates unique challenges and learning experiences for students in a lab practicum. Such educational kits containing the Zven1 or Zven2 gene, polypeptide, or antibody are considered within the scope of the present invention.

For any Zven polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise Zven1 or Zven2 variants based upon the nucleotide and amino acid sequences described herein. Accordingly, the present invention includes a computer-readable medium encoded with a data structure that provides at least one of the following sequences: SEQ ID NO:1, SEQ ID NO:2, SEQ ID NO:3, SEQ ID NO:4, SEQ ID NO:5, and SEQ ID NO:6. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

5. Production of Zven Fusion Proteins

Fusion proteins of Zven can be used to express a Zven polypeptide or peptide in a recombinant host, and to isolate expressed Zven polypeptides and peptides. One type of fusion protein comprises a peptide that guides a Zven polypeptide from a recombinant host cell. To direct a Zven polypeptide into the secretory pathway of a eukaryotic host cell, a secretory signal sequence (also known as a signal peptide, a leader sequence, prepro sequence or pre sequence) is provided in the Zven expression vector. While the secretory signal sequence may be derived from Zven1 or Zven2, a suitable signal sequence may also be derived from another secreted protein or synthesized de novo. The secretory signal sequence is operably linked to a Zven1- or Zven2-encoding sequence such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of Zven1, Zven2, or another protein produced by mammalian cells (e.g., tissue-type plasminogen activator signal sequence, as described, for example, in U.S. Pat. No. 5,641,655) is useful for expression of Zven1 or Zven2 in recombinant mammalian hosts, a yeast signal sequence is preferred for expression in yeast cells. Examples of suitable yeast signal sequences are those derived from yeast mating phermone α-factor (encoded by the MFα1 gene), invertase (encoded by the SUC2 gene), or acid phosphatase (encoded by the PHO5 gene). See, for example, Romanos et al., "Expression of Cloned Genes in Yeast," in *DNA Cloning 2: A Practical Approach*, $2^{nd}$ Edition, Glover and Hames (eds.), pages 123-167 (Oxford University Press 1995).

In bacterial cells, it is often desirable to express a heterologous protein as a fusion protein to decrease toxicity, increase stability, and to enhance recovery of the expressed protein. For example, Zven1 or Zven2 can be expressed as a fusion protein comprising a glutathione S-transferase polypeptide. Glutathione S-transferase fusion proteins are typically soluble, and easily purifiable from *E. coli* lysates on immobilized glutathione columns. In similar approaches, a Zven1 or Zven2 fusion protein comprising a maltose binding protein polypeptide can be isolated with an amylose resin column, while a fusion protein comprising the C-terminal end of a truncated Protein A gene can be purified using IgG-Sepharose. Established techniques for expressing a heterologous polypeptide as a fusion protein in a bacterial cell are described, for example, by Williams et al., "Expression of Foreign Proteins in *E. coli* Using Plasmid Vectors and Purification of Specific Polyclonal Antibodies," in *DNA Cloning 2: A Practical Approach*, $2^{nd}$ Edition, Glover and Hames (Eds.), pages 15-58 (Oxford University Press 1995). In addition, commercially available expression systems are available. For example, the PINPOINT Xa protein purification system (Promega Corporation; Madison, Wis.) provides a method for isolating a fusion protein comprising a polypeptide that becomes biotinylated during expression with a resin that comprises avidin.

Peptide tags that are useful for isolating heterologous polypeptides expressed by either prokaryotic or eukaryotic cells include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

Another form of fusion protein comprises a Zven1 or Zven2 polypeptide and an immunoglobulin heavy chain constant region, typically an $F_c$ fragment, which contains two constant region domains and a hinge region but lacks the variable region. As an illustration, Chang et al., U.S. Pat. No. 5,723,125, describe a fusion protein comprising a human interferon and a human immunoglobulin Fc fragment. The C-terminal of the interferon is linked to the N-terminal of the $F_C$ fragment by a peptide linker moiety. An example of a peptide linker is a peptide comprising primarily a T cell inert sequence, which is immunologically inert. An exemplary peptide linker has the amino acid sequence: GGSGG SGGGG SGGGG S (SEQ ID NO:7). In this fusion protein, a preferred Fc moiety is a human λ4 chain, which is stable in solution and has little or no complement activating activity. Accordingly, the present invention contemplates a Zven fusion protein that comprises a Zven1 or Zven2 polypeptide moiety and a human Fc fragment, wherein the C-terminus of the Zven polypeptide moiety is attached to the N-terminus of the Fc fragment via a peptide linker, such as a peptide consisting of the amino acid sequence of SEQ ID NO:7.

In another variation, a Zven1 or Zven2 fusion protein comprises an IgG sequence, a Zven polypeptide moiety covalently joined to the amino terminal end of the IgG sequence, and a signal peptide that is covalently joined to the amino terminal of the Zven polypeptide moiety, wherein the IgG sequence consists of the following elements in the following order: a hinge region, a $CH_2$ domain, and a $CH_3$ domain. Accordingly, the IgG sequence lacks a CH, domain. The Zven polypeptide moiety displays a Zven1 or Zven2 activity, such as the ability to bind with a Zven1 or Zven2 receptor. This general approach to producing fusion proteins that comprise both antibody and nonantibody portions has been described by LaRochelle et a., EP 742830 (WO 95/21258).

Fusion proteins comprising a Zven1 or Zven2 polypeptide moiety and an Fc moiety can be used, for example, as an in vitro assay tool. For example, the presence of a Zven1 or Zven2 receptor in a biological sample can be detected using these Zven1 or Zven2-antibody fusion proteins, in which the Zven moiety is used to target the cognate receptor, and a macromolecule, such as Protein A or anti-Fc antibody, is used to detect the bound fusion protein-ligand complex. In addition, antibody-Zven fusion proteins, comprising antibody variable domains, are useful as therapeutic proteins, in which the antibody moiety binds with a target antigen, such as a tumor associated antigen.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. General methods for enzymatic and chemical cleavage of fusion proteins are described, for example, by Ausubel (1995) at pages 16-19 to 16-25.

6. Production of Zven Polypeptides

The polypeptides of the present invention, including full-length polypeptides, functional fragments, and fusion proteins, can be produced in recombinant host cells following conventional techniques. To express a Zven1 or Zven2 gene, a nucleic acid molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene, which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, a Zven1 expression vector may comprise a Zven1 gene and a secretory sequence derived from a Zven1 gene or another secreted gene.

Zven1 or Zven2 proteins of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 [Chasin et al., *Som. Cell. Molec. Genet.* 12:555 1986]), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Nat'l Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice*, Cleland et al. (eds.), pages 163-181 (John Wiley & Sons, Inc. 1996)).

Alternatively, a prokaryotic promoter, such as the bacteriophage T3 RNA polymerase promoter, can be used to control Zven1 or Zven2 gene expression in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A suitable amplifiable selectable marker is dihydrofolate reductase, which confers resistance to methotrexate. Other drug resistance genes (e.g., hygromycin resistance, multi-drug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Zven1 or Zven2 polypeptides can also be produced by cultured mammalian cells using a viral delivery system. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161 (1994), and Douglas and Curiel, *Science &Medicine* 4:44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of protein (see Garnier et al., *Cytotechnol.* 15:145 (1994)).

Zven1 or Zven2 genes may also be expressed in other higher eukaryotic cells, such as avian, fungal, insect, yeast, or plant cells. The baculovirus system provides an efficient means to introduce cloned Zven1 or Zven2 genes into insect cells. Suitable expression vectors are based upon the *Autographa californica* multiple nuclear polyhedrosis virus (AcMNPV), and contain well-known promoters such as *Drosophila* heat shock protein (hsp) 70 promoter, *Autographa californica* nuclear polyhedrosis virus immediate-early gene promoter (ie-1) and the delayed early 39K promoter, baculovirus p10 promoter, and the *Drosophila* metallothionein promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the Zven polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed Zven polypeptide, for example, a Glu-Glu epitope tag (Grussenmeyer et al., *Proc. Nat'l Acad. Sci.* 82:7952 (1985)). Using a technique known in the art, a transfer vector containing a Zven1 or Zven2 gene is transformed into *E. coli*, and screened for bacmids, which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, *J. Gen. Virol.* 71:971 (1990), Bonning, et al., J Gen. Virol. 75:1551 (1994), and Chazenbalk and Rapoport, *J. Biol. Chem.* 270: 1543 (1995). In such transfer vector constructs, a short or long version of the basic protein promoter can be used. Moreover, transfer vectors can be constructed which replace the native Zven1/Zven2 secretory signal sequences with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to replace the native Zven1/Zven2 secretory signal sequence.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as *Drosophila* Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately 2-5× $10^5$ cells to a density of 1-2×$10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in *Methods in Molecular Biology*, Volume 7: *Gene Transfer and Expression Protocols*, Murray (ed.), pages 147-168 (The Humana Press, Inc. 1991), by Patel et al., "The baculovirus expression system," in *DNA Cloning 2: Expression Systems,* 2nd Edition, Glover et al. (eds.), pages 205-244 (Oxford University Press 1995), by Ausubel (1995) at pages 16-37 to 16-57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183-218 (John Wiley & Sons, Inc. 1996).

Fungal cells, including yeast cells, can also be used to express the genes described herein. Yeast species of particular interest in this regard include *Saccharomyces cerevisiae, Pichia pastoris,* and *Pichia methanolica.* Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et a., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A suitable vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615, 974, and Bitter, U.S. Pat. No. 4,977,092) and alcohol dehydrogenase genes. See also U.S. Pat. Nos. 4,990,446, 5,063, 154, 5,139,936, and 4,661,454.

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459 (1986), and Cregg, U.S. Pat. No. 4,882,279. *Aspergillus* cells may be utilized according to the methods of McKnight et al., U.S. Pat. No. 4,935,349. Methods for transforming *Acremonium*

*chrysogenum* are disclosed by Sumino et al., U.S. Pat. No. 5,162,228. Methods for transforming *Neurospora* are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11-23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which can be linearized prior to transformation. For polypeptide production in *P. methanolica*, the promoter and terminator in the plasmid can be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A suitable selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, it is possible to use host cells in which both methanol utilization genes (AUG1 and AUG2) are deleted. For production of secreted proteins, host cells can be used that are deficient in vacuolar protease genes (PEP4 and PRB1). Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., *Science* 227:1229 (1985), Klein et al., *Biotechnology* 10:268 (1992), and Miki et al., "Procedures for Introducing Foreign DNA into Plants," in *Methods in Plant Molecular Biology and Biotechnology*, Glick et al. (eds.), pages 67-88 (CRC Press, 1993).

Alternatively, Zven genes can be expressed in prokaryotic host cells. Suitable promoters that can be used to express Zven1 or Zven2 polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of *Bacillus, Streptomyces* promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277 (1987), Watson et al., *Molecular Biology of the Gene*, 4th Ed. (Benjamin Cummins 1987), and by Ausubel et al. (1995).

Suitable prokaryotic hosts include *E. coli* and *Bacillus subtilus*. Suitable strains of *E. coli* include BL21(DE3), BL21 (DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, MI120, and B170 (see, for example, Hardy, "Bacillus Cloning Methods," in *DNA Cloning: A Practical Approach*, Glover (ed.) (IRL Press 1985)).

When expressing a Zven polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning* 2: *Expression Systems,* 2nd Edition, Glover et al. (eds.), page 15 (Oxford University Press 1995), Ward et al., "Genetic Manipulation and Expression of Antibodies," in *Monoclonlal Antibodies: Principles andApplications*, page 137 (Wiley-Liss, Inc. 1995), and Georgiou, "Expression of Proteins in Bacteria," in *Protein Engineering: Principles and Practice*, Cleland et al. (eds.), page 101 (John Wiley & Sons, Inc. 1996)).

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning* 2: *Expression Systems,* 2nd Edition, Glover et al. (eds.), pages 59-92 (Oxford University Press 1995). Established methods for isolating recombinant proteins from a baculovirus system are described by Richardson (ed.), *Baculovirus Expression Protocols* (The Humana Press, Inc. 1995).

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, *J. Am. Chem. Soc.* 85:2149 (1963), Stewart et al., "Solid Phase Peptide Synthesis" (2nd Edition), (Pierce Chemical Co. 1984), Bayer and Rapp, *Chem. Pept. Prot.* 3:3 (1986), Atherton et al., *Solid Phase Peptide Synthesis: A Practical Approach* (IRL Press 1989), Fields and Colowick, "Solid-Phase Peptide Synthesis," *Methods in Enzymology* Volume 289 (Academic Press 1997), and Lloyd-Williams et al., *Chemical Approaches to the Synthesis of Peptides and Proteins* (CRC Press, Inc. 1997)). Variations in total chemical synthesis strategies, such as "native chemical ligation" and "expressed protein ligation"

are also standard (see, for example, Dawson et al., *Science* 266:776 (1994), Hackeng et al., *Proc. Nat'l Acad. Sci. USA* 94:7845 (1997), Dawson, *Methods Enzymol.* 287: 34 (1997), Muir et al, *Proc. Nat'l Acad. Sci. USA* 95:6705 (1998), and Severinov and Muir, *J. Biol. Chem.* 273:16205 (1998)).

Peptides and polypeptides of the present invention comprise at least six, at least nine, or at least 15 contiguous amino acid residues of SEQ ID NOs:2 and 5. Illustrative polypeptides of Zven2, for example, include 15 contiguous amino acid residues of amino acids 82 to 105 of SEQ ID NO:5. Exemplary polypeptides of Zven1 include 15 contiguous amino acid residues of amino acids 1 to 32 or amino acids 75 to 108 of SEQ ID NO:2, whereas exemplary Zven2 polypeptides include amino acids 82 to 105 of SEQ ID NO:5. Within certain embodiments of the invention, the polypeptides comprise 20, 30, 40, 50, 75, or more contiguous residues of SEQ ID NOs:2 or 5. Nucleic acid molecules encoding such peptides and polypeptides are useful as polymerase chain reaction primers and probes.

The present invention contemplates compositions comprising a peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

7. Isolation of Zven Polypeptides

The polypeptides of the present invention can be purified to at least about 80% purity, to at least about 90% purity, to at least about 95% purity, or even greater than 95% purity with respect to contaminating macromolecules, particularly other proteins and nucleic acids, and free of infectious and pyrogenic agents. The polypeptides of the present invention can also be purified to a pharmaceutically pure state, which is greater than 99.9% pure. In certain preparations, a purified polypeptide is substantially free of other polypeptides, particularly other polypeptides of animal origin.

Fractionation and/or conventional purification methods can be used to obtain preparations of Zven1 or Zven2 purified from natural sources, and recombinant Zven polypeptides and fusion Zven polypeptides purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, *Affinity Chromatography: Principles & Methods* (Pharmacia LKB Biotechnology 1988), and Doonan, *Protein Purification Protocols* (The Humana Press 1996).

Additional variations in Zven isolation and purification can be devised by those of skill in the art. For example, anti-Zven antibodies, obtained as described below, can be used to isolate large quantities of protein by immunoaffinity purification. Moreover, methods for binding receptors to ligand polypeptides, such as Zven1 or Zven2, bound to support media are well known in the art.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), *Meth. Enzymol.* 182:529 (1990)). Within additional embodiments of the invention, a fusion of the polypeptide of interest and an affinity tag (e.g., maltose-binding protein, an immunoglobulin domain) may be constructed to facilitate purification.

Zven polypeptides or fragments thereof may also be prepared through chemical synthesis, as described above. Zven polypeptides may be monomers or multimers; glycosylated or non-glycosylated; pegylated or non-pegylated; and may or may not include an initial methionine amino acid residue.

8. Zven Analogs and Zven Receptors

As described above, the disclosed polypeptides can be used to construct Zven variants. These polypeptides can be used to identify Zven1 or Zven2 analogs. One type of Zven analog mimics Zven by binding with a Zven receptor. Such an analog is considered to be a Zven agonist if the binding of the analog with a Zven receptor stimulates a response by a cell that expresses the receptor. On the other hand, a Zven analog that binds with a Zven receptor, but does not stimulate a cellular response, may be a Zven antagonist. Such an antagonist may diminish Zven or Zven agonist activity, for example, by a competitive or non-competitive binding of the antagonist to the Zven receptor.

One general class of Zven analogs are agonists or antagonists having an amino acid sequence that is a mutation of the amino acid sequences disclosed herein. Another general class of Zven analogs is provided by anti-idiotype antibodies, and fragments thereof, as described below. Moreover, recombinant antibodies comprising anti-idiotype variable domains can be used as analogs (see, for example, Monfardini et al., *Proc. Assoc. Am. Physicians* 108:420 (1996)). Since the variable domains of anti-idiotype Zven antibodies mimic Zven, these domains can provide either Zven agonist or antagonist activity. As an illustration, Lim and Langer, *J. Interferon Res.* 13:295 (1993), describe anti-idiotypic interferon-α antibodies that have the properties of either interferon-α agonists or antagonists.

A third approach to identifying Zven1 or Zven2 analogs is provided by the use of combinatorial libraries. Methods for constructing and screening phage display and other combinatorial libraries are provided, for example, by Kay et al., *Phage Display of Peptides and Proteins* (Academic Press 1996), Verdine, U.S. Pat. No. 5,783,384, Kay, et. al., U.S. Pat. No. 5,747,334, and Kauffman et al., U.S. Pat. No. 5,723,323.

Zven1, Zven2, their agonists and antagonists are valuable in both in vivo and in vitro uses. For example, Zven1, Zven2, or an agonist can be used as a component of defined cell culture media, alone or in combination with other bioactive agents, to replace serum that is commonly used in cell culture. For example, Zven proteins can be used to maintain in vitro models of spermatogenesis. Zven proteins can also be used to promote organ or tissue regeneration, to eliminate or to control cell proliferation, or to fabricate matrix elements within a vascular prosthesis, for example, to promote remodeling of vessels from an artificial vessel implant.

Antagonists are also useful as research reagents for characterizing sites of interaction between a Zven polypeptide and its receptor. In a therapeutic setting, pharmaceutical compositions comprising Zven antagonists can be used to inhibit Zven activity. As an illustration, Zven antagonists can be used to inhibit contraction of the ileum, and to decrease hyperalgesia.

The activity of a Zven polypeptide, agonist, or antagonist can be determined using a standard cell proliferation or differentiation assay. For example, assays measuring proliferation include such assays as chemosensitivity to neutral red dye, incorporation of radiolabeled nucleotides, incorporation of 5-bromo-2'-deoxyuridine in the DNA of proliferating cells, and use of tetrazolium salts (Mosmann, *J. Immunol. Methods* 65:55 (1983); Porstmann et al., *J. Immunol. Methods* 82:169 (1985); Alley et al., *Cancer Res.* 48:589 (1988); Cook et al., *Analytical Biochem.* 179:1 (1989); Marshall et al., *Growth Reg.* 5:69 (1995); Scudiero et al., *Cancer Res.* 48:4827 (1988); Cavanaugh et al., *Investigational New Drugs* 8:347 (1990)). Assays measuring differentiation include, for example, measuring cell-surface markers associated with stage-specific expression of a tissue, enzymatic activity, functional activity or morphological changes (Raes, *Adv. Anim. Cell Biol. Technol. Bioprocesses*, pages 161-171 (1989; Watt, *FASEB*, 5:281 (1991); Francis, *Differentiation* 57:63 (1994)). Assays can be used to measure other cellular responses, that include, chemotaxis, adhesion, changes in ion channel influx, regulation of second messenger levels and neurotransmitter release. Such assays are well known in the art (see, for example, Chayen and Bitensky, *Cytochemical Bioassays: Techniques & Applications* (Marcel Dekker 1983)).

The effect of a variant Zven polypeptide can also be determined by observing contractility of tissues, including gastrointestinal tissues, with tensiometer that measures contractility and relaxation in tissues (see, for example, Dainty et al., *J. Pharmacol.* 100:767 (1990); Rhee et al., *Neurotox.* 16:179 (1995); Anderson, *Endocrinol.* 114:364 (1984); Downing, and Sherwood, *Endocrinol.* 116:1206 (1985)). For example, methods for measuring vasodilatation of aortic rings are well known in the art. As an illustration, aortic rings are removed from four-month old Sprague Dawley rats and placed in a buffer solution, such as modified Krebs solution (118.5 mM NaCl, 4.6 mM KCl, 1.2 mM $MgSO_4.7H_2O$, 1.2 mM $KH_2PO_4$, 2.5 mM $CaCl_2.2H_2O$, 24.8 mM $NaHCO_3$ and 10 mM glucose). One of skill in the art would recognize that this method can be used with other animals, such as rabbits, other rat strains, Guinea pigs, and the like. The rings are then attached to an isometric force transducer (Radnoti Inc., Monrovia, Calif.) and the data are recorded with a Ponemah physiology platform (Gould Instrument systems, Inc., Valley View, Ohio) and placed in an oxygenated (95% $O_2$, 5% $CO_2$) tissue bath containing the buffer solution. The tissues are adjusted to one gram resting tension and allowed to stabilize for about one hour before testing. The integrity of the rings can be tested with norepinepherin (Sigma Co.; St. Louis, Mo.) and carbachol, a muscarinic acetylcholine agonist (Sigma Co.). After integrity is checked, the rings are washed three times with fresh buffer and allowed to rest for about one hour. To test a sample for vasodilatation, or relaxation of the aortic ring tissue, the rings are contracted to two grams tension and allowed to stabilize for fifteen minutes. A Zven polypeptide sample is then added to one, two, or three of the four baths, without flushing, and tension on the rings recorded and compared to the control rings containing buffer only. Enhancement or relaxation of contractility by Zven polypeptides, their agonists and antagonists is directly measured by this method, and it can be applied to other contractile tissues such as gastrointestinal tissues.

The effect of a variant Zven polypeptide on gastric motility would typically be measured in the clinical setting as the time required for gastric emptying and subsequent transit time through the gastrointestinal tract. Gastric emptying scans are well known to those skilled in the art, and briefly, comprise use of an oral contrast agent, such as barium, or a radiolabeled meal. Solids and liquids can be measured independently. Generally, a test food or liquid is radiolabeled with an isotope (e.g., $^{99m}Tc$), and after ingestion or administration, transit time through the gastrointestinal tract and gastric emptying are measured by visualization using gamma cameras (Meyer et al., *Am. J Dig. Dis.* 21:296 (1976); Collins et al., *Gut* 24:1117 (1983); Maughan et al., *Diabet. Med.* 13:S6 (1996), and Horowitz et al., *Arch. Intern. Med.* 145:1467 (1985)). These studies can be performed before and after the administration of a promotility agent to quantify the efficacy of the Zven polypeptide.

To determine if a variant Zven polypeptide is a chemotractant in vivo, the Zven polypeptide can be administered by intradermal or intraperitoneal injection. Characterization of the accumulated leukocytes at the site of injection can be determined using lineage specific cell surface markers and fluorescence immunocytometry or by immunohistochemistry (see, for example, Jose, *J. Exp. Med.* 179:881 (1994)). Release of specific leukocyte cell populations from bone marrow into peripheral blood can also be measured after Zven injection.

Zven1 or Zven2 polypeptides can be used to identify and to isolate their cognate receptors. For example, proteins and peptides of the present invention can be immobilized on a column and used to bind receptors from a biological sample that is run over the column (Hermanson et al. (eds.), *Immobilized Affinitn Ligand Techniques*, pages 195-202 (Academic Press 1992)). As a receptor ligand, the activity of Zven1 or Zven2 can be measured by a silicon-based biosensor microphysiometer, which measures the extracellular acidification rate or proton excretion associated with receptor binding and subsequent cellular responses. An exemplary device is the CYTOSENSOR Microphysiometer manufactured by Molecular Devices Corp. (Sunnyvale, Calif.). A variety of cellular responses, such as cell proliferation, ion transport, energy production, inflammatory response, regulatory and receptor activation, and the like, can be measured by this method (see, for example, McConnell et al., *Science* 257:1906 (1992), Pitchford et al., *Meth. Enzymol.* 228:84 (1997), Arimilli et al., *J. Immunol. Meth.* 212:49 (1998), and Van Liefde et al., *Eur. J Pharmacol.* 346:87 (1998)). Moreover, the microphysiometer can be used for assaying adherent or non-adherent eukaryotic or prokaryotic cells.

Since energy metabolism is coupled with the use of cellular ATP, any event, which alters cellular ATP levels, such as receptor activation and the initiation of signal transduction, will cause a change in cellular acid section. By measuring extracellular acidification changes in cell media over time, therefore, the microphysiometer directly measures cellular responses to various stimuli, including Zven1, Zven2, their agonists, or antagonists. The microphysiometer can be used to measure responses of a Zven-responsive eukaryotic cell, compared to a control eukaryotic cell that does not respond to a Zven polypeptide. Zven-responsive eukaryotic cells comprise cells into which a Zven receptor has been transfected to create a cell that is responsive to Zven, or cells that are naturally responsive to Zven. Zven-modulated cellular responses are measured by a change (e.g., an increase or decrease in extracellular acidification) in the response of cells exposed to Zven1 or Zven2, compared with control cells that have not been exposed to Zven1 or Zven2.

Accordingly, a microphysiometer can be used to identify cells, tissues, or cell lines which respond to a Zven-stimulated pathway, and which express a functional Zven receptor. As an illustration, cells that express a functional Zven1 receptor can be identified by (a) providing test cells, (b) incubating a first portion of the test cells in the absence of Zven1, (c) incubating a second portion of the test cells in the presence of Zven1, and (d) detecting a change (e.g., an increase or decrease in extracellular acidification rate, as measured by a microphysiometer) in a cellular response of the second portion of the test cells, as compared to the first portion of the test cells, wherein such a change in cellular response indicates that the test cells express a functional Zven1 receptor. An additional negative control may be included in which a portion of the test cells is incubated with Zven1 and an anti-Zven1 antibody to inhibit the binding of Zven1 with its cognate receptor. Similar approaches can be used to identify cells that express a functional Zven2 receptor Radiolabeled or affinity labeled Zven polypeptides can also be used to identify or to localize Zven receptors in a biological sample (see, for example, Deutscher (ed.), *Methods in Enzymol.*, vol. 182, pages 721-37 (Academic Press 1990); Brunner et al., *Ann. Rev. Biochem.* 62:483 (1993); Fedan et al., *Biochem. Pharmacol.* 33:1167 (1984)). Also see, Varthakavi and Minocha, *J Gen. Virol.* 77:1875 (1996), who describe the use of anti-idiotype antibodies for receptor identification.

A Zven polypeptide or Zven fusion protein can be immobilized onto the surface of a receptor chip of a commercially available biosensor instrument (BIACORE, Biacore AB; Uppsala, Sweden). The use of this instrument is disclosed, for example, by Karlsson, *Immunol. Methods* 145:229 (1991), and Cunningham and Wells, *J. Mol. Biol.* 234:554 (1993). This approach can be used to identify a Zven receptor, or an agonist or antagonist of a Zven receptor.

Zven1 or Zven2 receptor binding domains can be further characterized by physical analysis of structure, as determined by such techniques as nuclear magnetic resonance, crystallography, electron diffraction or photoaffinity labeling, in conjunction with mutation of putative contact site amino acids of Zven1 or Zven2 agonists. See, for example, de Vos et al., *Science* 255:306 (1992), Smith et al., *J. Mol. Biol.* 224:899 (1992), and Wlodaver et al., *FEBS Lett.* 309:59 (1992).

9. Production of Antibodies to Zven Proteins

Antibodies to a Zven polypeptide can be obtained, for example, using the product of a Zven expression vector or Zven isolated from a natural source as an antigen. Particularly useful anti-Zven1 and anti-Zven2 antibodies "bind specifically" with Zven1 and Zven2, respectively. Antibodies are considered to be specifically binding if the antibodies exhibit at least one of the following two properties: (1) antibodies bind to Zven1 or Zven2 with a threshold level of binding activity, and (2) antibodies do not significantly cross-react with polypeptides related to Zven1 or Zven2.

With regard to the first characteristic, antibodies specifically bind if they bind to a Zven polypeptide, peptide or epitope with a binding affinity ($K_a$) of $10^6 M^{-1}$ or greater, preferably $10^7 M^{-1}$ or greater, more preferably $10^8 M^{-1}$ or greater, and most preferably $10^9 M^{-1}$ or greater. The binding affinity of an antibody can be readily determined by one of ordinary skill in the art, for example, by Scatchard analysis (Scatchard, *Ann. NY Acad. Sci.* 51:660 (1949)). With regard to the second characteristic, antibodies do not significantly cross-react with related polypeptide molecules, for example, if they detect Zven, but not known polypeptides (e.g., known Wnt inhibitors) using a standard Western blot analysis. Particular anti-Zven1 antibodies bind Zven1, but not Zven2, while certain anti-Zven2 antibodies bind Zven2, but not Zven1.

Anti-Zven1 and anti-Zven2 antibodies can be produced using antigenic Zven1 or Zven2 epitope-bearing peptides and polypeptides. Antigenic epitope-bearing peptides and polypeptides of the present invention contain a sequence of at least four, or between 15 to about 30 amino acids contained within SEQ ID NOs:2 or 5. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with Zven1 or Zven2. It is desirable that the amino acid sequence of the epitope-bearing peptide is selected to provide substantial solubility in aqueous solvents (i.e., the sequence includes relatively hydrophilic residues, while hydrophobic residues are preferably avoided). Moreover, amino acid sequences containing proline residues may be also be desirable for antibody production.

As an illustration, potential antigenic sites in Zven1 or Zven2 were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The Jameson-Wolf method predicts potential antigenic determinants by combining six major subroutines for protein structural prediction. Briefly, the Hopp-Woods method, Hopp et al., *Proc. Nat'l Acad. Sci. USA* 78:3824 (1981), was first used to identify amino acid sequences representing areas of greatest local hydrophilicity (parameter: seven residues averaged). In the second step, Emini's method, Emini et al., *J. Virology* 55:836 (1985), was used to calculate surface probabilities (parameter: surface decision threshold (0.6)=1). Third, the Karplus-Schultz method, Karplus and Schultz, *Naturwissenschaften* 72:212 (1985), was used to predict backbone chain flexibility (parameter: flexibility threshold (0.2)=1). In the fourth and fifth steps of the analysis, secondary structure predictions were applied to the data using the methods of Chou-Fasman, Chou, "Prediction of Protein Structural Classes from Amino Acid Composition," in *Prediction of Protein Structure and the Principles of Protein Conformation*, Fasman (ed.), pages 549-586 (Plenum Press 1990), and Garnier-Robson, Garnier et al., *J. Mol. Biol.* 120:97 (1978) (Chou-Fasman parameters: conformation table=64 proteins; α region threshold=103; β region threshold=105; Garnier-Robson parameters: α and β decision constants=0). In the sixth subroutine, flexibility parameters and hydropathy/solvent accessibility factors were combined to determine a surface contour value, designated as the "antigenic index." Finally, a peak broadening function was applied to the antigenic index, which broadens major surface peaks by adding 20, 40, 60, or 80% of the respective peak value to account for additional free energy derived from the mobility of surface regions relative to interior regions. This calculation was not applied, however, to any major peak that resides in a helical region, since helical regions tend to be less flexible.

The results of this analysis indicated that suitable antigenic peptides of Zven1 include the following segments of the amino acid sequence of SEQ ID NO:2: amino acids 22 to 27 ("antigenic peptide 1"), amino acids 33 to 41 ("antigenic peptide 2"), amino acids 61 to 68 ("antigenic peptide 3"), amino acids 80 to 85 ("antigenic peptide 4"), amino acids 97 to 102 ("antigenic peptide 5"), and amino acids 61 to 85 ("antigenic peptide 6"). The present invention contemplates the use of any one of antigenic peptides 1 to 6 to generate antibodies to Zven1. The present invention also contemplates polypeptides comprising at least one of antigenic peptides 1 to 6.

Similarly, analysis of the Zven2 amino acid sequence indicated that suitable antigenic peptides of Zven2 include the following segments of the amino acid sequence of SEQ ID NO:5: amino acids 25 to 33 ("antigenic peptide 7"), amino acids 53 to 66 ("antigenic peptide 8"), amino acids 88 to 95 ("antigenic peptide 9"), amino acids 98 to 103 ("antigenic peptide 10"), and amino acids 88 to 103 ("antigenic peptide 11"). The present invention contemplates the use of any one of antigenic peptides 7 to 11 to generate antibodies to Zven2. The present invention also contemplates polypeptides comprising at least one of antigenic peptides 7 to 11.

Polyclonal antibodies to recombinant Zven protein or to Zven isolated from natural sources can be prepared using methods well-known to those of skill in the art. See, for example, Green et al., "Production of Polyclonal Antisera," in *Immunochemical Protocols* (Manson, ed.), pages 1-5 (Humana Press 1992), and Williams et al., "Expression of foreign proteins in *E. coli* using plasmid vectors and purification of specific polyclonal antibodies," in *DNA Cloning* 2: *Expression Systems,* 2nd Edition, Glover et al. (eds.), page 15 (Oxford University Press 1995). The immunogenicity of a Zven polypeptide can be increased through the use of an adjuvant, such as alum (aluminum hydroxide) or Freund's complete or incomplete adjuvant. Polypeptides useful for immunization also include fusion polypeptides, such as fusions of Zven or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, guinea pigs, goats, or sheep, an anti-Zven antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310 (1990).

Alternatively, monoclonal anti-Zven antibodies can be generated. Rodent mono-clonal antibodies to specific antigens may be obtained by methods known to those skilled in the art (see, for example, Kohler et al., *Nature* 256:495 (1975), Coligan et al. (eds.), *Current Protocols in Immunology,* Vol. 1, pages 2.5.1-2.6.7 (John Wiley & Sons 1991) ["Coligan"], Picksley et al., "Production of monoclonal antibodies against proteins expressed in *E. coli,*" in *DNA Cloning* 2: *Expression Systems,* 2nd Edition, Glover et al. (eds.), page 93 (Oxford University Press 1995)).

Briefly, monoclonal antibodies can be obtained by injecting mice with a composition comprising a Zven gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-Zven antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13 (1994), Lonberg et al., *Nature* 368:856 (1994), and Taylor et al., *Int. Immun.* 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology,* Vol. 10, pages 79-104 (The Humana Press, Inc. 1992)).

For particular uses, it may be desirable to prepare fragments of anti-Zven antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology* Vol. 1, page 422 (Academic Press 1967), and by Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659

(1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains, which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector, which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11:1271 (1993), and Sandhu, supra).

As an illustration, a scFV can be obtained by exposing lymphocytes to Zven polypeptide in vitro, and selecting antibody display libraries in phage or similar vectors (for instance, through use of immobilized or labeled Zven protein or peptide). Genes encoding polypeptides having potential Zven polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides, which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et a., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the Zven sequences disclosed herein to identify proteins which bind to Zven.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-Zven antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989). Techniques for producing humanized monoclonal antibodies are described, for example, by Jones et al., *Nature* 321:522 (1986), Carter et al., *Proc. Nat'l Acad. Sci. USA* 89:4285 (1992), Sandhu, *Crit. Rev. Biotech.* 12:437 (1992), Singer et al., *J. Immun.* 150:2844 (1993), Sudhir (ed.), *Antibody Engineering Protocols* (Humana Press, Inc. 1995), Kelley, "Engineering Therapeutic Antibodies," in *Protein Engineering: Principles and Practice*, Cleland et al. (eds.), pages 399-434 (John Wiley & Sons, Inc. 1996), and by Queen et al., U.S. Pat. No. 5,693,762 (1997).

Polyclonal anti-idiotype antibodies can be prepared by immunizing animals with anti-Zven antibodies or antibody fragments, using standard techniques. See, for example, Green et al., "Production of Polyclonal Antisera," in *Methods In Molecular Biology: Immunochemical Protocols*, Manson (ed.), pages 1-12 (Humana Press 1992). Also, see Coligan at pages 2.4.1-2.4.7. Alternatively, monoclonal anti-idiotype antibodies can be prepared using anti-Zven antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875 (1996).

10. Detection of Zven Gene Expression and Examination of the Zven Chromosomal Locus Nucleic acid molecules can be used to detect the expression of a Zven1 or Zven2 gene in a biological sample. Such probe molecules include double-stranded nucleic acid molecules comprising the nucleotide sequence of SEQ ID NOs:1 or 4, or a fragment thereof, as well as single-stranded nucleic acid molecules having the complement of the nucleotide sequence of SEQ ID NOs:1 or 4, or a fragment thereof. Probe molecules may be DNA, RNA, oligonucleotides, and the like.

Illustrative probes comprise a portion of the nucleotide sequence of nucleotides 66 to 161 of SEQ ID NO:1, the nucleotide sequence of nucleotides 288 to 389 of SEQ ID NO:1, the nucleotide sequence of nucleotides 334 to 405 of SEQ ID NO:4, or to the complement of such nucleotide sequences. An additional example of a suitable probe is a probe consisting of nucleotides 354 to 382 of SEQ ID NO:1, or a portion thereof. As used herein, the term "portion" refers to at least eight nucleotides to at least 20 or more nucleotides.

For example, nucleic acid molecules comprising a portion of the nucleotide sequence of SEQ ID NO:1 can be used to detect activated neutrophils. Such molecules can also be used to identity therapeutic or prophylactic agents that modulate the response of a neutrophil to a pathogen.

In a detection basic assay, a single-stranded probe molecule is incubated with RNA, isolated from a biological sample, under conditions of temperature and ionic strength that promote base pairing between the probe and target Zven RNA species. After separating unbound probe from hybridized molecules, the amount of hybrids is detected.

Well-established hybridization methods of RNA detection include northern analysis and dot/slot blot hybridization (see, for example, Ausubel (1995) at pages 4-1 to 4-27, and Wu et al. (eds.), "Analysis of Gene Expression at the RNA Level," in *Methods in Gene Biotechnology*, pages 225-239 (CRC Press, Inc. 1997)). Nucleic acid probes can be detectably labeled with radioisotopes such as $^{32}$P or $^{35}$S. Alternatively, Zven RNA can be detected with a nonradioactive hybridization method (see, for example, Isaac (ed.), *Protocols for Nucleic Acid Analysis by Nonradioactive Probes* (Humana Press, Inc. 1993)). Typically, nonradioactive detection is achieved by enzymatic conversion of chromogenic or chemiluminescent substrates. Illustrative nonradioactive moieties include biotin, fluorescein, and digoxigenin.

Zven oligonucleotide probes are also useful for in vivo diagnosis. As an illustration, $^{18}$F-labeled oligonucleotides can be administered to a subject and visualized by positron emission tomography (Tavitian et al., *Nature Medicine* 4:467 (1998)).

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

One variation of PCR for diagnostic assays is reverse transcriptase-PCR (RT-PCR). In the RT-PCR technique, RNA is isolated from a biological sample, reverse transcribed to cDNA, and the cDNA is incubated with Zven primers (see, for example, Wu et al. (eds.), "Rapid Isolation of Specific cDNAs or Genes by PCR," in *Methods in Gene Biotechnology*, pages 15-28 (CRC Press, Inc. 1997)). PCR is then performed and the products are analyzed using standard techniques.

As an illustration, RNA is isolated from biological sample using, for example, the guanidinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or Zven anti-sense oligomers. Oligo-dT primers offer the advantage that various mRNA nucleotide sequences are amplified that can provide control target sequences. Zven sequences are amplified by the polymerase chain reaction using two flanking oligonucleotide primers that are typically 20 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled Zven probe, and examined by autoradiography. Additional alternative approaches include the use of digoxigenin-labeled deoxyribonucleic acid triphosphates to provide chemiluminescence detection, and the C-TRAK colorimetric assay.

Another approach for detection of Zven1 or Zven2 expression is cycling probe technology (CPT), in which a single-stranded DNA target binds with an excess of DNA-RNA-DNA chimeric probe to form a complex, the RNA portion is cleaved with RNAase H, and the presence of cleaved chimeric probe is detected (see, for example, Beggs et al., *J. Clin. Microbiol.* 34:2985 (1996), Bekkaoui et al., *Biotechniques* 20:240 (1996)). Alternative methods for detection of Zven sequences can utilize approaches such as nucleic acid sequence-based amplification (NASBA), cooperative amplification of templates by cross-hybridization (CATCH), and the ligase chain reaction (LCR) (see, for example, Marshall et al., U.S. Pat. No. 5,686,272 (1997), Dyer et al., *J. Virol. Methods* 60:161 (1996), Ehricht et al., *Eur. J Biochem.* 243:358 (1997), and Chadwick et a., *J. Virol. Methods* 70:59 (1998)). Other standard methods are known to those of skill in the art.

Zven probes and primers can also be used to detect and to localize Zven gene expression in tissue samples. Methods for such in situ hybridization are well-known to those of skill in the art (see, for example, Choo (ed.), *In Situ Hybridization Protocols* (Humana Press, Inc. 1994), Wu et al. (eds.), "Analysis of Cellular DNA or Abundance of mRNA by Radioactive In Situ Hybridization (RISH)," in *Methods in Gene Biotechnology*, pages 259-278 (CRC Press, Inc. 1997), and Wu et al. (eds.), "Localization of DNA or Abundance of mRNA by Fluorescence In Situ Hybridization (RISH)," in *Methods in Gene Biotechnology*, pages 279-289 (CRC Press, Inc. 1997)). Various additional diagnostic approaches are well-known to those of skill in the art (see, for example, Mathew (ed.), *Protocols in Human Molecular Genetics* (Humana Press, Inc. 1991), Coleman and Tsongalis, *Molecular Diagnostics* (Humana Press, Inc. 1996), and Elles, *Molecular Diagnosis of Genetic Diseases* (Humana Press, Inc., 1996)).

The Zven2 gene was found to reside at human chromosome 1p13; the Wnt2B gene also resides in this region, as well as differentiation genes CSF1 and Notch2. Chromosome 1p13 is associated with various diseases and disorders, including retinitis pigmentosa, Stargardt disease, Waardenburg syndrome, nemaline myopathy, Kabuki syndrome, and cardiomyopathy. The Zven1 gene resides in human chromosome 3p21.1-3p14.3. This region of chromosome 3 is associated with metaphyseal chondrodysplasia, small cell cancer of the lung, cerebral gigantism (Sotos Syndrome), Larsen Syndrome, spinocerebellar ataxia, Wernicke-Korsakoff Syndrome, hyperglycinemia, septooptic dysplasia, progressive external ophthalmoplegia, and pancreatic cancer. The Wnt5A gene also resides in this region.

Nucleic acid molecules comprising Zven nucleotide sequences can be used to determine whether a subject's chromosomes contain a mutation in the Zven gene. Detectable chromosomal aberrations at the Zven1 or Zven2 gene locus include, but are not limited to, aneuploidy, gene copy number changes, insertions, deletions, restriction site changes and rearrangements. Of particular interest are genetic alterations that inactivate a Zven1 or Zven2 gene.

Aberrations associated with a Zven1 or Zven2 locus can be detected using nucleic acid molecules of the present invention by employing molecular genetic techniques, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocolsfor Mutation Detection* (Oxford University Press 1996), Birren et al. (eds.), *Genome Analysis*, Vol. 2: *Detecting Genes* (Cold Spring Harbor Laboratory Press 1998), Dracopoli et al. (eds.), *Current Protocols in Human Genetics* (John Wiley &

Sons 1998), and Richards and Ward, "Molecular Diagnostic Testing," in *Principles of Molecular Medicine*, pages 83-88 (Humana Press, Inc. 1998)).

The protein truncation test is also useful for detecting the inactivation of a gene in which translation-terminating mutations produce only portions of the encoded protein (see, for example, Stoppa-Lyonnet et al., *Blood* 91:3920 (1998)). According to this approach, RNA is isolated from a biological sample, and used to synthesize cDNA. PCR is then used to amplify the Zven target sequence and to introduce an RNA polymerase promoter, a translation initiation sequence, and an in-frame ATG triplet. PCR products are transcribed using an RNA polymerase, and the transcripts are translated in vitro with a T7-coupled reticulocyte lysate system. The translation products are then fractionated by SDS-PAGE to determine the lengths of the translation products. The protein truncation test is described, for example, by Dracopoli et al. (eds.), *Current Protocols in Human Genetics*, pages 9.11.1-9.11.18 (John Wiley & Sons 1998).

The present invention also contemplates kits for performing a diagnostic assay for Zven1 or Zven2 gene expression or to examine a Zven locus. Such kits comprise nucleic acid probes, such as double-stranded nucleic acid molecules comprising the nucleotide sequence of SEQ ID NOs:1 or 4, or a fragment thereof, as well as single-stranded nucleic acid molecules having the complement of the nucleotide sequence of SEQ ID NOs:1 or 4, or a fragment thereof. Probe molecules may be DNA, RNA, oligonucleotides, and the like. Kits may comprise nucleic acid primers for performing PCR.

Such a kit can contain all the necessary elements to perform a nucleic acid diagnostic assay described above. A kit will comprise at least one container comprising a Zven probe or primer. The kit may also comprise a second container comprising one or more reagents capable of indicating the presence of Zven sequences. Examples of such indicator reagents include detectable labels such as radioactive labels, fluorochromes, chemiluminescent agents, and the like. A kit may also comprise a means for conveying to the user that the Zven probes and primers are used to detect Zven gene expression. For example, written instructions may state that the enclosed nucleic acid molecules can be used to detect either a nucleic acid molecule that encodes Zven, or a nucleic acid molecule having a nucleotide sequence that is complementary to a Zven-encoding nucleotide sequence. The written material can be applied directly to a container, or the written material can be provided in the form of a packaging insert.

11. Detection of Zven Protein with Anti-Zven Antibodies

The present invention contemplates the use of anti-Zven antibodies to screen biological samples in vitro for the presence of Zven1 or Zven2. In one type of in vitro assay, anti-Zven antibodies are used in liquid phase. For example, the presence of Zven in a biological sample can be tested by mixing the biological sample with a trace amount of labeled Zven1 (or Zven2) and an anti-Zven antibody under conditions that promote binding between Zven and its antibody. Complexes of Zven and anti-Zven in the sample can be separated from the reaction mixture by contacting the complex with an immobilized protein which binds with the antibody, such as an Fc antibody or *Staphylococcus* protein A. The concentration of Zven in the biological sample will be inversely proportional to the amount of labeled Zven bound to the antibody and directly related to the amount of free labeled Zven.

Alternatively, in vitro assays can be performed in which anti-Zven antibody is bound to a solid-phase carrier. For example, antibody can be attached to a polymer, such as aminodextran, in order to link the antibody to an insoluble support such as a polymer-coated bead, a plate or a tube. Other suitable in vitro assays will be readily apparent to those of skill in the art.

In another approach, anti-Zven antibodies can be used to detect Zven1 or Zven2 in tissue sections prepared from a biopsy specimen. Such immunochemical detection can be used to determine the relative abundance of Zven and to determine the distribution of Zven in the examined tissue. General immunochemistry techniques are well established (see, for example, Ponder, "Cell Marking Techniques and Their Application," in *Mammalian Development: A Practical Approach*, Monk (ed.), pages 115-38 (IRL Press 1987), Coligan at pages 5.8.1-5.8.8, Ausubel (1995) at pages 14.6.1 to 14.6.13 (Wiley Interscience 1990), and Manson (ed.), *Methods In Molecular Biology, Vol.* 10: *Immunochemical Protocols* (The Humana Press, Inc. 1992)).

Immunochemical detection can be performed by contacting a biological sample with an anti-Zven antibody, and then contacting the biological sample with a detectably labeled molecule which binds to the antibody. For example, the detectably labeled molecule can comprise an antibody moiety that binds to anti-Zven antibody. Alternatively, the anti-Zven antibody can be conjugated with avidin/streptavidin (or biotin) and the detectably labeled molecule can comprise biotin (or avidin/streptavidin). Numerous variations of this basic technique are well-known to those of skill in the art.

Alternatively, an anti-Zven antibody can be conjugated with a detectable label to form an anti-Zven immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3H$, $^{125}I$, $^{131}I$, $^{35}S$ and $^{14}C$.

Anti-Zven immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-Zven immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-Zven immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-Zven immunoconjugates can be detectably labeled by linking an anti-Zven antibody component to an enzyme. When the anti-Zven-enzyme conjugate is incubated in the presence of the appropriate substrate, the enzyme moiety reacts with the substrate to produce a chemical moiety, which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels, which can be employed in accordance with the present invention. The binding of marker moieties to anti-Zven antibodies can be accomplished using standard techniques known to the art. Typical methodology in this regard is described by Kennedy et al, *Clin. Chim. Acta* 70:1 (1976), Schurs et al, *Clin. Chim. Acta* 81:1 (1977), Shih et al., Int'l Cancer 46:1101(1990), Stein et al., *Cancer Res.* 50:1330(1990), and Coligan, supra.

Moreover, the convenience and versatility of immunochemical detection can be enhanced by using anti-Zven antibodies that have been conjugated with avidin, streptavidin, and biotin (see, for example, Wilchek et a. (eds.), "Avidin-Biotin Technology," *Methods In Enzymology*, Vol. 184 (Academic Press 1990), and Bayer et a., "Immunochemical Applications of Avidin-Biotin Technology," in *Methods In Molecular Biology*, Vol. 10, Manson (ed.), pages 149-162 (The Humana Press, Inc. 1992).

Methods for performing immunoassays are well-established. See, for example, Cook and Self, "Monoclonal Antibodies in Diagnostic Immunoassays," in *Monoclonal Antibodies: Production, Engineering, and Clinical Application*, Ritter and Ladyman (eds.), pages 180-208, (Cambridge University Press, 1995), Perry, "The Role of Monoclonal Antibodies in the Advancement of Immunoassay Technology," in *Monoclonal Antibodies: Principles and Applications*, Birch and Lennox (eds.), pages 107-120 (Wiley-Liss, Inc. 1995), and Diamandis, *Immunoassay (Academic Press, Inc.* 1996).

In a related approach, biotin- or FITC-labeled Zven1 or Zven2 can be used to identify cells that bind Zven1 or Zven2. Such can binding can be detected, for example, using flow cytometry.

The present invention also contemplates kits for performing an immunological diagnostic assay for Zven gene expression. Such kits comprise at least one container comprising an anti-Zven antibody, or antibody fragment. A kit may also comprise a second container comprising one or more reagents capable of indicating the presence of Zven antibody or antibody fragments. Examples of such indicator reagents include detectable labels such as a radioactive label, a fluorescent label, a chemiluminescent label, an enzyme label, a bioluminescent label, colloidal gold, and the like. A kit may also comprise a means for conveying to the user that Zven antibodies or antibody fragments are used to detect Zven protein. For example, written instructions may state that the enclosed antibody or antibody fragment can be used to detect Zven. The written material can be applied directly to a container, or the written material can be provided in the form of a packaging insert.

12. Therapeutic Uses of Zven Polypeptides

The present invention includes the use of proteins, polypeptides, and peptides having Zven activity (such as Zven polypeptides, Zven analogs, active Zven anti-idiotype antibodies, and Zven fusion proteins) to a subject, which lacks an adequate amount of this polypeptide. The present invention contemplates both veterinary and human therapeutic uses. Illustrative subjects include mammalian subjects, such as farm animals, domestic animals, and human patients.

For example, a protein, a polypeptide, or a peptide having Zven1 activity can be administered to a subject (e.g., a human patient), which has small cell cancer of the lung. In contrast, Zven antagonists (e.g., anti-Zven antibodies or anti-Zven anti-idiotype antibodies that are biologically inactive) can be used to treat a subject who produces an excess of Zven. Therapeutic uses for Zven proteins include, anti-tumor agent (e.g., anti-lung tumor agent), anti-inflammatory agent, an agent to regulate regeneration or remodeling of tissues, and an agent to modulate necrosis or tissue growth developmental arrest. As an illustration, Zven polypeptides may be used to promote wound healing, to prevent or to treat an adverse reaction of the skin to a skin-sensitizing agent or a skin-irritating agent, or to stimulate the immune system of an immunocompromised individual.

For example, polypeptides, peptides, and peptides having Zven2 activity may be used to inhibit cellular proliferation, cellular differentiation, and necrosis. In particular, polypeptides, peptides, and peptides having Zven2 activity may be used to inhibit cellular proliferation associated with mammary tumors, colon cancer, melanomas, hepatocellular carcinomas, and the like.

The Zven polypeptides of the present invention may also be used in treatment of disorders associated with gastrointestinal cell contractility, secretion of digestive enzymes and acids, gastrointestinal motility, recruitment of digestive enzymes; inflammation, particularly as it affects the gastrointestinal system; and reflux disease and regulation of nutrient absorption; and modulation of blood pressure. Specific conditions that will benefit from treatment with molecules of the present invention include, but are not limited to, diabetic gastroparesis, post-surgical gastroparesis, vagotomy, chronic idiopathic intestinal pseudo-obstruction and gastroesophageal reflux disease. Additional uses include, gastric emptying for radiological studies, stimulating gallbladder contraction and antrectomy. Zven antagonists are useful for clinical conditions associated with gastrointestinal hypermotility such as diarrhea and Crohn's disease.

Generally, the dosage of administered polypeptide, protein or peptide will vary depending upon such factors as the patient's age, weight, height, sex, general medical condition and previous medical history. Typically, it is desirable to provide the recipient with a dosage of a molecule having Zven activity, which is in the range of from about 1 pg/kg to 10 mg/kg (amount of agent/body weight of patient), although a lower or higher dosage also may be administered as circumstances dictate.

Administration of a molecule having Zven activity to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses. Alternatively, Zven1 or Zven2 can be administered as a controlled release formulation.

Additional routes of administration include oral, dermal, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising Zven1 or Zven2 can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., *Science* 269: 850 (1995)). Transdermal delivery using electroporation provides another means to administer Zven1 or Zven2 (Potts et al., *Pharm. Biotechnol.* 10:213 (1997)).

Zven proteins can also be applied topically as, for example, liposomal preparations, gels, salves, as a component of a glue, prosthesis, or bandage, and the like. Topical administration is useful for wound healing applications, including the prevention of excess scaring and granulation tissue, prevention of keyloids, and prevention of adhesions following surgery.

A pharmaceutical composition comprising molecules having Zven1 or Zven2 activity can be furnished in liquid form, in an aerosol, or in solid form. Proteins having Zven1 or Zven2 activity can be administered as a conjugate with a pharmaceutically acceptable water-soluble polymer moiety. As an illustration, a Zven1-polyethylene glycol conjugate is useful to increase the circulating half-life of the interferon, and to reduce the immunogenicity of the polypeptide. Liquid forms, including liposome-encapsulated formulations, are illustrated by injectable solutions and oral suspensions. Exemplary solid forms include capsules, tablets, and controlled-release forms, such as a miniosmotic pump or an implant. Other dosage forms can be devised by those skilled in the art, as shown, for example, by Ansel and Popovich, *Pharmaceutical Dosage Forms and Drug Delivery Systems,* $5^{th}$ Edition (Lea & Febiger 1990), Gennaro (ed.), *Remington's Pharmaceutical Sciences,* $19^{th}$ Edition (Mack Publishing Company 1995), and by Ranade and Hollinger, *Drug Delivery Systems* (CRC Press 1996).

A pharmaceutical composition comprising a protein, polypeptide, or peptide having Zven1 or Zven2 activity can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences,* 19th Edition (Mack Publishing Company 1995).

For purposes of therapy, molecules having Zven1 or Zven2 activity and a pharmaceutically acceptable carrier are administered to a patient in a therapeutically effective amount. A combination of a protein, polypeptide, or peptide having Zven activity and a pharmaceutically acceptable carrier is said to be administered in a "therapeutically effective amount" if the amount administered is physiologically significant. An agent is physiologically significant if its presence results in a detectable change in the physiology of a recipient patient.

For example, the present invention includes methods of inhibiting the proliferation of tumor cells, comprising the step of administering a composition comprising a Zven2 polypeptide or peptide to the tumor cells. In an in vivo approach, the composition is a pharmaceutical composition, administered in a therapeutically effective amount to a mammalian subject, which has a tumor. Such in vivo administration can provide at least one physiological effect selected from the group consisting of decreased number of tumor cells, decreased metastasis, decreased size of a solid tumor, and increased necrosis of a tumor.

A pharmaceutical composition comprising molecules having Zven activity can be furnished in liquid form, or in solid form. Liquid forms, including liposome-encapsulated formulations, are illustrated by injectable solutions and oral suspensions. Exemplary solid forms include capsules, tablets, and controlled-release forms, such as a miniosmotic pump or an implant. Other dosage forms can be devised by those skilled in the art, as shown, for example, by Ansel and Popovich, *Pharmaceutical Dosage Forms and Drug Delivery Systems,* $5^{th}$ Edition (Lea & Febiger 1990), Gennaro (ed.), *Remington's Pharmaceutical Sciences,* $19^{th}$ Edition (Mack Publishing Company 1995), and by Ranade and Hollinger, *Drug Delivery Systems* (CRC Press 1996).

Zven1 or Zven2 pharmaceutical compositions may be supplied as a kit comprising a container that comprises Zven1 or Zven2, a Zven1 or Zven2 agonist, or a Zven1 or Zven2 antagonist (e.g., an anti-Zven1 or Zven2 antibody or antibody fragment). For example, Zven1 or Zven2 can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the Zven1 or Zven2 composition is contraindicated in patients with known hypersensitivity to Zven1 or Zven2.

13. Therapeutic Uses of Zven Nucleotide Sequences

The present invention includes the use of Zven nucleotide sequences to provide Zven amino acid sequences to a subject in need of proteins, polypeptides, or peptides having Zven activity, as discussed in the previous section. For example, Zven2 nucleotide sequences can be used to produce Zven2 in order to inhibit cellular proliferation. In addition, a therapeutic expression vector can be provided that inhibits Zven gene expression, such as an anti-sense molecule, a ribozyme, or an external guide sequence molecule.

There are numerous approaches to introduce a Zven gene to a subject, including the use of recombinant host cells that express Zven, delivery of naked nucleic acid encoding Zven, use of a cationic lipid carrier with a nucleic acid molecule that encodes Zven, and the use of viruses that express Zven, such as recombinant retroviruses, recombinant adeno-associated viruses, recombinant adenoviruses, and recombinant Herpes simplex viruses [HSV] (see, for example, Mulligan, *Science* 260:926 (1993), Rosenberg et al., *Science* 242:1575 (1988), LaSalle et al., *Science* 259:988 (1993), Wolff et al., *Science* 247:1465 (1990), Breakfield and Deluca, *The New Biologist* 3:203 (1991)). In an ex vivo approach, for example, cells are isolated from a subject, transfected with a vector that expresses a Zven gene, and then transplanted into the subject.

In order to effect expression of a Zven gene, an expression vector is constructed in which a nucleotide sequence encoding a Zven gene is operably linked to a core promoter, and optionally a regulatory element, to control gene transcription. The general requirements of an expression vector are described above.

Alternatively, a Zven gene can be delivered using recombinant viral vectors, including for example, adenoviral vectors (e.g., Kass-Eisler et al., *Proc. Nat'l Acad. Sci. USA* 90:11498 (1993), Kolls et al., *Proc. Nat'l Acad. Sci. USA* 91:215 (1994), Li et al., *Hum. Gene Ther.* 4:403 (1993), Vincent et al., *Nat. Genet.* 5:130 (1993), and Zabner et al., *Cell* 75:207 (1993)), adenovirus-associated viral vectors (Flotte et al., *Proc. Nat'l Acad. Sci. USA* 90:10613 (1993)), alphaviruses such as Semliki Forest Virus and Sindbis Virus (Hertz and Huang, *J. Vir.* 66:857 (1992), Raju and Huang, *J. Vir.* 65:2501 (1991), and Xiong et al., *Science* 243:1188 (1989)), herpes viral vectors (e.g., U.S. Pat. Nos. 4,769,331, 4,859,587, 5,288,641 and 5,328,688), parvovirus vectors (Koering et al., *Hum. Gene Therap.* 5:457 (1994)), pox virus vectors (Ozaki et al., *Biochem. Biophys. Res. Comm.* 193:653 (1993), Panicali and Paoletti, *Proc. Nat'l Acad. Sci. USA* 79:4927 (1982)), pox viruses, such as canary pox virus or vaccinia virus (Fisher-Hoch et al., *Proc. Nat'l Acad. Sci. USA* 86:317 (1989), and Flexner et al., *Ann. N.Y. Acad. Sci.* 569:86 (1989)), and retroviruses (e.g., Baba et al., *J. Neurosurg* 79:729 (1993), Ram et al., *Cancer Res.* 53:83 (1993), Takamiya et al., *J. Neurosci. Res* 33:493 (1992), Vile and Hart, *Cancer Res.* 53:962 (1993), Vile and Hart, *Cancer Res.* 53:3860 (1993), and Anderson et al., U.S. Pat. No. 5,399,346). Within various embodiments, either the viral vector itself, or a viral particle which contains the viral vector may be utilized in the methods and compositions described below.

As an illustration of one system, adenovirus, a double-stranded DNA virus, is a well-characterized gene transfer vector for delivery of a heterologous nucleic acid molecule (for a review, see Becker et al., *Meth. Cell Biol.* 43:161 (1994); Douglas and Curiel, *Science & Medicine* 4:44 (1997)). The adenovirus system offers several advantages including: (i) the ability to accommodate relatively large DNA inserts, (ii) the ability to be grown to high-titer, (iii) the ability to infect a broad range of mammalian cell types, and (iv) the ability to be used with many different promoters including ubiquitous, tissue specific, and regulatable promoters. In addition, adenoviruses can be administered by intravenous injection, because the viruses are stable in the bloodstream.

Using adenovirus vectors where portions of the adenovirus genome are deleted, inserts are incorporated into the viral DNA by direct ligation or by homologous recombination with a co-transfected plasmid. In an exemplary system, the essential E1 gene is deleted from the viral vector, and the virus will not replicate unless the E1 gene is provided by the host cell. When intravenously administered to intact animals, adenovirus primarily targets the liver. Although an adenoviral delivery system with an E1 gene deletion cannot replicate in the host cells, the host's tissue will express and process an encoded heterologous protein. Host cells will also secrete the heterologous protein if the corresponding gene includes a secretory signal sequence. Secreted proteins will enter the circulation from tissue that expresses the heterologous gene (e.g., the highly vascularized liver).

Moreover, adenoviral vectors containing various deletions of viral genes can be used to reduce or eliminate immune responses to the vector. Such adenoviruses are E1-deleted, and in addition, contain deletions of E2A or E4 (Lusky et al., *J. Virol.* 72:2022 (1998); Raper et al., *Human Gene Therapy* 9:671 (1998)). The deletion of E2b has also been reported to reduce immune responses (Amalfitano et al., *J. Virol.* 72:926 (1998)). By deleting the entire adenovirus genome, very large inserts of heterologous DNA can be accommodated. Generation of so called "gutless" adenoviruses, where all viral genes are deleted, are particularly advantageous for insertion of large inserts of heterologous DNA (for a review, see Yeh. and Perricaudet, *FASEB J.* 11:615 (1997)).

High titer stocks of recombinant viruses capable of expressing a therapeutic gene can be obtained from infected mammalian cells using standard methods. For example, recombinant HSV can be prepared in Vero cells, as described by Brandt et al., *J. Gen. Virol.* 72:2043 (1991), Herold et al., *J. Gen. Virol.* 75:1211 (1994), Visalli and Brandt, *Virology* 185:419 (1991), Grau et al., *Invest. Ophthalmol. Vis. Sci.* 30:2474 (1989), Brandt et al., *J. Virol. Meth.* 36:209 (1992), and by Brown and MacLean (eds.), *HSV Virus Protocols* (Humana Press 1997).

Alternatively, an expression vector comprising a Zven gene can be introduced into a subject's cells by lipofection in vivo using liposomes. Synthetic cationic lipids can be used to prepare liposomes for in vivo transfection of a gene encoding a marker (Felgner et al., *Proc. Nat'l Acad. Sci. USA* 84:7413 (1987); Mackey et al., *Proc. Nat'l Acad. Sci. USA* 85:8027 (1988)). The use of lipofection to introduce exogenous genes into specific organs in vivo has certain practical advantages. Liposomes can be used to direct transfection to particular cell types, which is particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Electroporation is another alternative mode of administration of Zven nucleic acid molecules. For example, Aihara and Miyazaki, *Nature Biotechnology* 16:867 (1998), have demonstrated the use of in vivo electroporation for gene transfer into muscle.

In an alternative approach to gene therapy, a therapeutic gene may encode a Zven anti-sense RNA that inhibits the expression of Zven. Suitable sequences for Zven anti-sense molecules can be derived from the nucleotide sequences of Zven disclosed herein.

Alternatively, an expression vector can be constructed in which a regulatory element is operably linked to a nucleotide sequence that encodes a ribozyme. Ribozymes can be designed to express endonuclease activity that is directed to a certain target sequence in a mRNA molecule (see, for example, Draper and Macejak, U.S. Pat. No. 5,496,698, McSwiggen, U.S. Pat. No. 5,525,468, Chowrira and McSwiggen, U.S. Pat. No. 5,631,359, and Robertson and Goldberg, U.S. Pat. No. 5,225,337). In the context of the present invention, ribozymes include nucleotide sequences that bind with Zven mRNA.

In another approach, expression vectors can be constructed in which a regulatory element directs the production of RNA transcripts capable of promoting RNase P-mediated cleavage of mRNA molecules that encode a Zven gene. According to this approach, an external guide sequence can be constructed for directing the endogenous ribozyme, RNase P, to a particular species of intracellular mRNA, which is subsequently cleaved by the cellular ribozyme (see, for example, Altman et al., U.S. Pat. No. 5,168,053, Yuan et al., *Science* 263:1269 (1994), Pace et al., international publication No. WO 96/18733, George et al., international publication No. WO 96/21731, and Werner et al., international publication No. WO 97/33991). Preferably, the external guide sequence comprises a ten to fifteen nucleotide sequence complementary to Zven mRNA, and a 3'-NCCA nucleotide sequence, wherein N is preferably a purine. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

In general, the dosage of a composition comprising a therapeutic vector having a Zven nucleotide acid sequence, such as a recombinant virus, will vary depending upon such factors as the subject's age, weight, height, sex, general medical condition and previous medical history. Suitable routes of administration of therapeutic vectors include intravenous injection, intraarterial injection, intraperitoneal injection, intramuscular injection, intratumoral injection, and injection into a cavity that contains a tumor.

A composition comprising viral vectors, non-viral vectors, or a combination of viral and non-viral vectors of the present invention can be formulated according to known methods to prepare pharmaceutically useful compositions, whereby vectors or viruses are combined in a mixture with a pharmaceutically acceptable carrier. As noted above, a composition, such as phosphate-buffered saline is said to be a "pharmaceutically acceptable carrier" if its administration can be tolerated by a recipient subject. Other suitable carriers are well-known to those in the art (see, for example, *Remington's Pharmaceutical Sciences*, 19th Ed. (Mack Publishing Co. 1995), and *Gilman's the Pharmacological Basis of Therapeutics*, 7th Ed. (MacMillan Publishing Co. 1985)).

For purposes of therapy, a therapeutic gene expression vector, or a recombinant virus comprising such a vector, and a pharmaceutically acceptable carrier are administered to a subject in a therapeutically effective amount. A combination of an expression vector (or virus) and a pharmaceutically acceptable carrier is said to be administered in a "therapeutically effective amount" if the amount administered is physiologically significant. An agent is physiologically significant if its presence results in a detectable change in the physiology of a recipient subject.

When the subject treated with a therapeutic gene expression vector or a recombinant virus is a human, then the therapy is preferably somatic cell gene therapy. That is, the preferred treatment of a human with a therapeutic gene expression vector or a recombinant virus does not entail introducing into cells a nucleic acid molecule that can form part of a human germ line and be passed onto successive generations (i.e., human germ line gene therapy).

14. Production of Transgenic Mice

Transgenic mice can be engineered to over-express the Zven gene in all tissues or under the control of a tissue-specific or tissue-preferred regulatory element. These over-producers of Zven can be used to characterize the phenotype that results from over-expression, and the transgenic animals can serve as models for human disease caused by excess Zven. Transgenic mice that over-express Zven also provide model bioreactors for production of Zven in the milk or blood of larger animals. Methods for producing transgenic mice are well-known to those of skill in the art (see, for example, Jacob, "Expression and Knockout of Interferons in Transgenic Mice," in *Overexpression and Knockout of Cytokines in Transgenic Mice*, Jacob (ed.), pages 111-124 (Academic Press, Ltd. 1994), Monastersky and Robl (eds.), Strategies in Transgenic Animal Science (ASM Press 1995), and Abbud and Nilson, "Recombinant Protein Expression in Transgenic Mice," in *Gene Expression Systems: Using Nature for the Art of Expression*, Fernandez and Hoeffler (eds.), pages 367-397 (Academic Press, Inc. 1999)).

For example, a method for producing a transgenic mouse that expresses a Zven gene can begin with adult, fertile males (studs) (B6C3f1, 2-8 months of age (Taconic Farms, Germantown, N.Y.)), vasectomized males (duds) (B6D2f1, 2-8 months, (Taconic Farms)), prepubescent fertile females (donors) (B6C3f1, 4-5 weeks, (Taconic Farms)) and adult fertile females (recipients) (B6D2f1, 2-4 months, (Taconic Farms)). The donors are acclimated for one week and then injected with approximately 8 IU/mouse of Pregnant Mare's Serum gonadotrophin (Sigma Chemical Company; St. Louis, Mo.) I.P., and 46-47 hours later, 8 IU/mouse of human Chorionic Gonadotropin (hCG (Sigma)) I.P. to induce superovulation. Donors are mated with studs subsequent to hormone injections. Ovulation generally occurs within 13 hours of hCG injection. Copulation is confirmed by the presence of a vaginal plug the morning following mating.

Fertilized eggs are collected under a surgical scope. The oviducts are collected and eggs are released into urinanalysis slides containing hyaluronidase (Sigma). Eggs are washed once in hyaluronidase, and twice in Whitten's W640 medium (described, for example, by Menino and O'Claray, *Biol. Reprod.* 77:159 (1986), and Dienhart and Downs, *Zygote* 4:129 (1996)) that has been incubated with 5% $CO_2$, 5% $O_2$, and 90% $N_2$ at 37° C. The eggs are then stored in a 37° C./5% $CO_2$ incubator until microinjection.

Ten to twenty micrograms of plasmid DNA containing a Zven encoding sequence is linearized, gel-purified, and resuspended in 10 mM Tris-HCl (pH 7.4), 0.25 mM EDTA (pH 8.0), at a final concentration of 5-10 nanograms per microliter for microinjection. For example, the Zven1 encoding sequences can comprise nucleotide sequences that encode amino acid residues 23 to 108 of SEQ ID NO:2, while Zven2 encoding sequences can encode a polypeptide comprising amino acid residues 148 to 405 of SEQ ID NO:5.

Plasmid DNA is microinjected into harvested eggs contained in a drop of W640 medium overlaid by warm, $CO_2$-equilibrated mineral oil. The DNA is drawn into an injection needle (pulled from a 0.75 mm ID, 1 mm OD borosilicate glass capillary), and injected into individual eggs. Each egg is penetrated with the injection needle, into one or both of the haploid pronuclei.

Picoliters of DNA are injected into the pronuclei, and the injection needle withdrawn without coming into contact with the nucleoli. The procedure is repeated until all the eggs are injected. Successfully microinjected eggs are transferred into an organ tissue-culture dish with pre-gassed W640 medium for storage overnight in a 37° C./5% $CO_2$ incubator.

The following day, two-cell embryos are transferred into pseudopregnant recipients. The recipients are identified by the presence of copulation plugs, after copulating with vasectomized duds. Recipients are anesthetized and shaved on the dorsal left side and transferred to a surgical microscope. A small incision is made in the skin and through the muscle wall in the middle of the abdominal area outlined by the ribcage, the saddle, and the hind leg, midway between knee and spleen. The reproductive organs are exteriorized onto a small surgical drape. The fat pad is stretched out over the surgical drape, and a baby serrefine (Roboz, Rockville, Md.) is attached to the fat pad and left hanging over the back of the mouse, preventing the organs from sliding back in.

With a fine transfer pipette containing mineral oil followed by alternating W640 and air bubbles, 12-17 healthy two-cell embryos from the previous day's injection are transferred into the recipient. The swollen ampulla is located and holding the oviduct between the ampulla and the bursa, a nick in the oviduct is made with a 28 g needle close to the bursa, making sure not to tear the ampulla or the bursa.

The pipette is transferred into the nick in the oviduct, and the embryos are blown in, allowing the first air bubble to escape the pipette. The fat pad is gently pushed into the peritoneum, and the reproductive organs allowed to slide in. The peritoneal wall is closed with one suture and the skin closed with a wound clip. The mice recuperate on a 37° C. slide warmer for a minimum of four hours.

The recipients are returned to cages in pairs, and allowed 19-21 days gestation. After birth, 19-21 days postpartum is allowed before weaning. The weanlings are sexed and placed into separate sex cages, and a 0.5 cm biopsy (used for genotyping) is snipped off the tail with clean scissors.

Genomic DNA is prepared from the tail snips using, for example, a QIAGEN DNEASY kit following the manufacturer's instructions. Genomic DNA is analyzed by PCR using primers designed to amplify a Zven gene or a selectable marker gene that was introduced in the same plasmid. After animals are confirmed to be transgenic, they are back-crossed into an inbred strain by placing a transgenic female with a wild-type male, or a transgenic male with one or two wild-type female(s). As pups are born and weaned, the sexes are separated, and their tails snipped for genotyping.

To check for expression of a transgene in a live animal, a partial hepatectomy is performed. A surgical prep is made of the upper abdomen directly below the zyphoid process. Using sterile technique, a small 1.5-2 cm incision is made below the sternum and the left lateral lobe of the liver exteriorized. Using 4-0 silk, a tie is made around the lower lobe securing it outside the body cavity. An atraumatic clamp is used to hold the tie while a second loop of absorbable Dexon (American Cyanamid; Wayne, N.J.) is placed proximal to the first tie. A distal cut is made from the Dexon tie and approximately 100 mg of the excised liver tissue is placed in a sterile petri dish. The excised liver section is transferred to a 14 ml polypropylene round bottom tube and snap frozen in liquid nitrogen and then stored on dry ice. The surgical site is closed with suture and wound clips, and the animal's cage placed on a 37° C. heating pad for 24 hours post operatively. The animal is checked daily post operatively and the wound clips removed 7-10 days after surgery. The expression level of Zven mRNA is examined for each transgenic mouse using an RNA solution hybridization assay or polymerase chain reaction.

In addition to producing transgenic mice that over-express Zven, it is useful to engineer transgenic mice with either abnormally low or no expression of the gene. Such transgenic mice provide useful models for diseases associated with a lack of Zven. As discussed above, Zven gene expression can be inhibited using anti-sense genes, ribozyme genes, or external guide sequence genes. To produce transgenic mice that under-express the Zven gene, such inhibitory sequences are targeted to Zven mRNA. Methods for producing transgenic mice that have abnormally low expression of a particular gene are known to those in the art (see, for example, Wu et al., "Gene Underexpression in Cultured Cells and Animals by Antisense DNA and RNA Strategies," in Methods in Gene Biotechnology, pages 205-224 (CRC Press 1997)).

An alternative approach to producing transgenic mice that have little or no Zven gene expression is to generate mice having at least one normal Zven allele replaced by a nonfunctional Zven gene. One method of designing a nonfunctional Zven gene is to insert another gene, such as a selectable marker gene, within a nucleic acid molecule that encodes Zven. Standard methods for producing these so-called "knockout mice" are known to those skilled in the art (see, for example, Jacob, "Expression and Knockout of Interferons in Transgenic Mice," in *Overexpression and Knockout of Cytokines in Transgenic Mice*, Jacob (ed.), pages 111-124 (Academic Press, Ltd. 1994), and Wu et al., "New Strategies for Gene Knockout," in *Methods in Gene Biotechnology*, pages 339-365 (CRC Press 1997)).

The present invention, thus generally described, will be understood more readily by reference to the following examples, which are provided by way of illustration and are not intended to be limiting of the present invention.

EXAMPLE 1

Expression of the Zven1 Gene

Zven1 gene expression was examined using a PCR array panel of cell lines, including blood cell and connective tissue cell lines. In one study, Zven1 expression was found to be restricted to B cell, T cell, monocyte, and granulocyte cell lines. Zven1 appeared to be highly expressed in the promyelocytic cell line HL60. This observation indicates that Zven1 is expressed in blood progenitor cells, because the HL60 line is capable of differentiating into either monocytes or granulocytes. The only tested nonhematopoietic line displaying Zven1 expression was A549, a lung adenocarcinoma line.

In another study, freshly isolated human neutrophils and monocytes were screened via PCR for Zven1 expression with or without lipopolysaccharide (LPS) activation. Zven1 gene expression was detected in unactivated monocytes, but not in activated monocytes. Expression was also apparent in granulocytes. Zven1 expression was not detected in endothelial cells of a microvascular origin.

EXAMPLE 2

Inhibition of Cellular Proliferation by Zven1

The effect of Zven1 on cellular proliferation was examined using conditioned media either from cells infected with an adenovirus vector designed to express Zven1, or from cells infected with an adenovirus vector that lacked a Zven1 gene (parental control). In one study, human fibroblast cells from normal lung (ATCC NO. CRL-1490) were plated at 2500 cells/100 □l/well in 96 well plates with normal growth medium (MEM with Earle's salts and NEAA, 10% fetal bovine serum (FBS)). After plating, the cells were allowed to adhere to the plates for 24 hours. Media were then discarded, and conditioned media test samples diluted in growth media were added (100 □l/well). For comparison, murine Lewis Lung carcinoma cells (8000 cells per well in 10 □l) were transferred into 96 well plates, which contained 100 □l/well of conditioned media test samples diluted in growth media (DMEM high glucose, 10% FBS). All cells were incubated for 72 hours.

After 72 hours, cells were examined using the CellTiter 96R Non-Radioactive Cell Proliferation Assay (Promega Corporation; Madison, Wis.). Absorbance readings were measured at A572-A650. Percent inhibition values were calculated as the average of triplicate readings of A572-A650, using the equation: 100-((100*Abs of sample)/Abs of medium alone). The results indicated that Zven1 can inhibit the proliferation of Lewis Lung cells by about 50% below controls, whereas Zven 1 treatment appeared to inhibit the proliferation of normal lung cells by about 10%.

The ability of Zven1 to affect the proliferation of A549 human lung adenocarcinoma cells was tested with conditioned media. A549 cells are plated at 1,000 cells per well in Hams F12 containing 10%FBS, and incubated for three days prior to serum starvation in Hams F12 (without FBS) for 24 hours. Zven1 conditioned media samples were diluted 1:1 with either serum-free media or media containing 10% FBS, and proliferation was measured after a 72 hour incubation. The results of this study indicated that Zven1 can inhibit the proliferation of A549 cells below controls by about 25%.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated nucleic acid molecule that encodes a polypeptide consisting of amino acid residues 23 to 108 of SEQ ID NO:2.

2. An isolated nucleic acid molecule comprising nucleotides 288 to 389 of SEQ ID NO:1.

3. The isolated nucleic acid molecule of claim 2, wherein the nucleic acid molecule consists of nucleotides 288 to 389 of SEQ ID NO:1.

4. The isolated nucleic acid molecule of claim 2, wherein the nucleic acid molecule consists of nucleotides 132 to 389 of SEQ ID NO:1.

5. An isolated nucleic acid molecule comprising nucleotides 66 to 161 of SEQ ID NO:1.

6. The isolated nucleic acid molecule of claim 5, wherein the nucleic acid molecule consists of nucleotides 66 to 161 of SEQ ID NO:1.

7. A vector, comprising (a) the isolated nucleic acid molecule that encodes a polypeptide consisting of amino acid residues 23 to 108 of SEQ ID NO:2; (b) the isolated nucleic acid molecule comprising nucleotides 132 to 389 of SEQ ID NO:1; (c) the isolated nucleic acid molecule comprising nucleotides 288 to 389 of SEQ ID NO:1; or (d) the isolated nucleic acid molecule comprising nucleotides 66 to 161 of SEQ ID NO:1.

8. An isolated recombinant host cell, comprising an expression vector, wherein the expression vector comprises one of: the nucleic acid molecules of claim 7, a transcription promoter, and a transcription terminator, wherein the promoter is operably linked with the nucleic acid molecule, and the nucleic acid molecule is operably linked with the transcription terminator, wherein the host cell is selected from the group consisting of bacterium, yeast cell, fungal cell, insect cell, avian cell, mammalian cell, and plant cell.

9. The recombinant host cell of claim 8, wherein the host cell is a bacterium.

10. A method of producing a polypeptide comprising culturing the recombinant host cells of claim 8, wherein the polypeptide is produced.

11. The method of claim 10, further comprising the step of isolating the polypeptide from the cultured recombinant host cell.

* * * * *

SEQUENCE LISTING

<160> NUMBER OF SEQ ID NOS: 9

<210> SEQ ID NO 1
<211> LENGTH: 1496
<212> TYPE: DNA
<213> ORGANISM: Homo sapiens
<220> FEATURE:
<221> NAME/KEY: CDS
<222> LOCATION: (66)...(389)

<400> SEQUENCE: 1

```
cgcccttact cactataggg ctcgagcggc cgcccgggca ggtgccgccc agtcccgagg      60 gcgcc atg agg agc ctg tgc tgc gcc cca ctc ctg ctc ctc ttg ctg ctg     110
      Met Arg Ser Leu Cys Cys Ala Pro Leu Leu Leu Leu Leu Leu Leu
      1               5                   10                  15 ccg ccg ctg ctc ctc acg ccc cgc gct ggg gac gcc gcc gtg atc acc      158
Pro Pro Leu Leu Leu Thr Pro Arg Ala Gly Asp Ala Ala Val Ile Thr
                20                  25                  30 ggg gct tgt gac aag gac tcc caa tgt ggt gga ggc atg tgc tgt gct      206
Gly Ala Cys Asp Lys Asp Ser Gln Cys Gly Gly Gly Met Cys Cys Ala
            35                  40                  45 gtc agt atc tgg gtc aag agc ata agg att tgc aca cct atg ggc aaa      254
Val Ser Ile Trp Val Lys Ser Ile Arg Ile Cys Thr Pro Met Gly Lys
    50                  55                  60 ctg gga gac agc tgc cat cca ctg act cgt aaa gtt cca ttt ttt ggg      302
Leu Gly Asp Ser Cys His Pro Leu Thr Arg Lys Val Pro Phe Phe Gly
65                  70                  75 cgg agg atg cat cac act tgc cca tgt ctg cca ggc ttg gcc tgt tta      350
Arg Arg Met His His Thr Cys Pro Cys Leu Pro Gly Leu Ala Cys Leu
80                  85                  90                  95 cgg act tca ttt aac cga ttt att tgt tta gcc caa aag taatcgctct      399
Arg Thr Ser Phe Asn Arg Phe Ile Cys Leu Ala Gln Lys
                100                 105 ggagtagaaa ccaaatgtga atagccacat cttacctgta aagtcttact tgtgattgtg     459
ccaaacaaaa aatgtgccag aaagaaatgc tcttgcttcc tcaactttcc aagtaacatt     519
tttatctttg atttgtaaat gattttttt tttttttta tcgaaagaga attttacttt      579
tggatagaaa tatgaagtgt aaggcattat ggaactggtt cttatttccc tgtttgtgtt     639
ttggtttgat ttggcttttt tcttaaatgt caaaaacgta cccatttca caaaaatgag      699 gaaaataaga atttgatatt tgttagaaa aactttttt ttttttctc accaccccaa       759 gccccatttg tgccctgccg cacaaataca cctacagctt ttggtccctt gcctcttcca     819
cctcaaagaa tttcaaggct cttaccttac tttatttttg tccatttctc ttccctcctc     879
ttgcatttta aagtggaggg tttgtctctt tgagtttgat ggcagaatca ctgatgggaa     939
tccagctttt tgctggcatt taaatagtga aaagagtgta tatgtgaact tgacactcca     999
aactcctgtc atggcacgga agctaggagt gctgctggac ccttcctaaa cctgtcactc    1059
aagaggactt cagctctgct gttgggctgg tgtgtggaca gaaggaatgg aaagccaaat    1119
taatttagtc cagatttcta ggtttgggtt tttctaaaaa taaagatta catttacttc     1179 ttttactttt tataaagttt tttttcctta gtctcctact tagagatatt ctagaaaatg    1239
tcacttgaag aggaagtatt tattttaatc tggcacaaca ctaattacca tttttaaagc    1299
ggtattaagt tgtaatttaa accttgtttg taactgaaag gtcgattgta atggattgcc    1359
gtttgtacct gtatcagtat tgctgtgtaa aaattctgta tcagaataat aacagtactg    1419
```

```
tatatcattt gatttatttt aatattatat ccttatttttt gtcaaaaaaa aaaaaaaaa      1479 aaaaatatgc ggccgcg                                                    1496

<210> SEQ ID NO 2
<211> LENGTH: 108
<212> TYPE: PRT
<213> ORGANISM: Homo sapiens

<400> SEQUENCE: 2

Met Arg Ser Leu Cys Cys Ala Pro Leu Leu Leu Leu Leu Pro
 1               5                  10                  15

Pro Leu Leu Leu Thr Pro Arg Ala Gly Asp Ala Ala Val Ile Thr Gly
                20                  25                  30

Ala Cys Asp Lys Asp Ser Gln Cys Gly Gly Met Cys Cys Ala Val
            35                  40                  45

Ser Ile Trp Val Lys Ser Ile Arg Ile Cys Thr Pro Met Gly Lys Leu
        50                  55                  60

Gly Asp Ser Cys His Pro Leu Thr Arg Lys Val Pro Phe Phe Gly Arg
65                  70                  75                  80

Arg Met His His Thr Cys Pro Cys Leu Pro Gly Leu Ala Cys Leu Arg
                85                  90                  95

Thr Ser Phe Asn Arg Phe Ile Cys Leu Ala Gln Lys
            100                 105

<210> SEQ ID NO 3
<211> LENGTH: 324
<212> TYPE: DNA
<213> ORGANISM: Artificial Sequence
<220> FEATURE:
<223> OTHER INFORMATION: This degenerate sequence encodes the amino acid
      sequence of SEQ ID NO:2.
<220> FEATURE:
<221> NAME/KEY: misc_feature
<222> LOCATION: (1)...(324)
<223> OTHER INFORMATION: n = A,T,C or G

<400> SEQUENCE: 3
atgmgnwsny tntgytgygc nccnytnytn ytnytnytny tnytnccncc nytnytnytn       60
acnccnmgng cnggngaygc ngcngtnath acnggngcnt gygayaarga ywsncartgy      120
ggnggnggna tgtgytgygc ngtnwsnath tgggtnaarw snathmgnat htgyacnccn      180
atgggnaary tnggngayws ntgycayccn ytnacnmgna argtnccntt yttyggnmgn      240
mgnatgcayc ayacntgycc ntgyytnccn ggnytngcnt gyytnmgnac nwsnttyaay      300
mgnttyatht gyytngcnca raar                                            324

<210> SEQ ID NO 4
<211> LENGTH: 1409
<212> TYPE: DNA
<213> ORGANISM: Homo sapiens
<220> FEATURE:
<221> NAME/KEY: CDS
<222> LOCATION: (91)...(405)

<400> SEQUENCE: 4
tggcctcccc agcttgccag gcacaaggct gagcgggagg aagcgagagg catctaagca       60
ggcagtgttt tgccttcacc ccaagtgacc atg aga ggt gcc acg cga gtc tca      114
                                 Met Arg Gly Ala Thr Arg Val Ser
                                  1               5 atc atg ctc ctc cta gta act gtg tct gac tgt gct gtg atc aca ggg       162
Ile Met Leu Leu Leu Val Thr Val Ser Asp Cys Ala Val Ile Thr Gly
```

```
                   10                  15                  20
gcc tgt gag cgg gat gtc cag tgt ggg gca ggc acc tgc tgt gcc atc      210
Ala Cys Glu Arg Asp Val Gln Cys Gly Ala Gly Thr Cys Cys Ala Ile
 25                  30                  35                  40 agc ctg tgg ctt cga ggg ctg cgg atg tgc acc ccg ctg ggg cgg gaa      258
Ser Leu Trp Leu Arg Gly Leu Arg Met Cys Thr Pro Leu Gly Arg Glu
                 45                  50                  55 ggc gag gag tgc cac ccc ggc agc cac aag gtc ccc ttc ttc agg aaa      306
Gly Glu Glu Cys His Pro Gly Ser His Lys Val Pro Phe Phe Arg Lys
                 60                  65                  70 cgc aag cac cac acc tgt cct tgc ttg ccc aac ctg ctg tgc tcc agg      354
Arg Lys His His Thr Cys Pro Cys Leu Pro Asn Leu Leu Cys Ser Arg
             75                  80                  85 ttc ccg gac ggc agg tac cgc tgc tcc atg gac ttg aag aac atc aat      402
Phe Pro Asp Gly Arg Tyr Arg Cys Ser Met Asp Leu Lys Asn Ile Asn
         90                  95                 100 ttt taggcgcttg cctggtctca ggatacccac catccttttc ctgagcacag           455
Phe
105 cctggatttt tatttctgcc atgaaaccca gctcccatga ctctcccagt ccctacactg    515 actaccctga tctctcttgt ctagtacgca catatgcaca caggcagaca tacctcccat    575 catgacatgg tccccaggct ggcctgagga tgtcacagct tgaggctgtg gtgtgaaagg    635 tggccagcct ggttctcttc cctgctcagg ctgccagaga ggtggtaaat ggcagaaagg    695 acattccccc tcccctcccc aggtgacctg ctctcttttcc tgggccctgc ccctctcccc   755 acatgtatcc ctcggtctga attagacatt cctgggcaca ggctcttggg tgcattgctc    815 agagtcccag gtcctggcct gaccctcagg cccttcacgt gaggtctgtg aggaccaatt    875 tgtgggtagt tcatcttccc tcgattggtt aactccttag tttcagacca cagactcaag    935 attggctctt cccagagggc agcagacagt caccccaagg caggtgtagg gagcccaggg    995 aggccaatca gcccctgaa gactctggtc ccagtcagcc tgtggcttgt ggcctgtgac    1055 ctgtgacctt ctgccagaat tgtcatgcct ctgaggcccc ctcttaccac actttaccag   1115 ttaaccactg aagcccccaa ttcccacagc ttttccatta aaatgcaaat ggtggtggtt   1175 caatctaatc tgatattgac atattagaag gcaattaggg tgtttcctta acaactcct    1235 ttccaaggat cagccctgag agcaggttgg tgactttgag gagggcagtc ctctgtccag   1295 attggggtgg gagcaaggga cagggagcag ggcaggggct gaaagggca ctgattcaga    1355 ccagggaggc aactacacac caacctgctg gctttagaat aaaagcacca actg         1409
```

<210> SEQ ID NO 5
<211> LENGTH: 105
<212> TYPE: PRT
<213> ORGANISM: Homo sapiens

<400> SEQUENCE: 5

Met Arg Gly Ala Thr Arg Val Ser Ile Met Leu Leu Leu Val Thr Val
 1               5                  10                  15

Ser Asp Cys Ala Val Ile Thr Gly Ala Cys Glu Arg Asp Val Gln Cys
                 20                  25                  30

Gly Ala Gly Thr Cys Cys Ala Ile Ser Leu Trp Leu Arg Gly Leu Arg
             35                  40                  45

Met Cys Thr Pro Leu Gly Arg Glu Gly Glu Glu Cys His Pro Gly Ser
         50                  55                  60

His Lys Val Pro Phe Phe Arg Lys Arg Lys His His Thr Cys Pro Cys 65                  70                  75                  80
Leu Pro Asn Leu Leu Cys Ser Arg Phe Pro Asp Gly Arg Tyr Arg Cys
                    85                  90                  95

Ser Met Asp Leu Lys Asn Ile Asn Phe
            100                 105

<210> SEQ ID NO 6
<211> LENGTH: 315
<212> TYPE: DNA
<213> ORGANISM: Artificial Sequence
<220> FEATURE:
<223> OTHER INFORMATION: This degenerate sequence encodes the amino acid
      sequence of SEQ ID NO:5.
<220> FEATURE:
<221> NAME/KEY: misc_feature
<222> LOCATION: (1)...(315)
<223> OTHER INFORMATION: n = A,T,C or G

<400> SEQUENCE: 6
atgmgnggng cnacnmgngt nwsnathatg ytnytnytng tnacngtnws ngaytgygcn      60
gtnathacng gngcntgyga rmgngaygtn cartgyggng cnggnacntg ytgygcnath    120
wsnytntggy tnmgnggnyt nmgnatgtgy acnccnytng gnmgngargg ngargartgy    180
cayccnggnw sncayaaargt nccnttytty mgnaarmgna arcaycayac ntgyccntgy    240
ytnccnaayy tnytntgyws nmgnttyccn gayggnmgnt aymgntgyws natggayytn    300
aaraayatha aytty                                                     315

<210> SEQ ID NO 7
<211> LENGTH: 16
<212> TYPE: PRT
<213> ORGANISM: Artificial Sequence
<220> FEATURE:
<223> OTHER INFORMATION: Peptide linker.

<400> SEQUENCE: 7

Gly Gly Ser Gly Gly Ser Gly Gly Gly Ser Gly Gly Gly Gly Ser
1               5                  10                  15

<210> SEQ ID NO 8
<211> LENGTH: 10
<212> TYPE: PRT
<213> ORGANISM: Artificial Sequence
<220> FEATURE:
<223> OTHER INFORMATION: Motif.
<220> FEATURE:
<221> NAME/KEY: VARIANT
<222> LOCATION: (8)...(8)
<223> OTHER INFORMATION: Xaa is Asp or Glu.
<220> FEATURE:
<221> NAME/KEY: VARIANT
<222> LOCATION: (9)...(9)
<223> OTHER INFORMATION: Xaa is Lys or Arg.

<400> SEQUENCE: 8

Ala Val Ile Thr Gly Ala Cys Xaa Xaa Asp
1               5                  10

<210> SEQ ID NO 9
<211> LENGTH: 23
<212> TYPE: PRT
<213> ORGANISM: Artificial Sequence
<220> FEATURE:
<223> OTHER INFORMATION: Motif.
<220> FEATURE:
<221> NAME/KEY: VARIANT
<222> LOCATION: (4)...(4)

```
-continued

<223> OTHER INFORMATION: Xaa is Gly or Leu.
<220> FEATURE:
<221> NAME/KEY: VARIANT
<222> LOCATION: (5) . . . (5)
<223> OTHER INFORMATION: Xaa is Ser or Thr.
<220> FEATURE:
<221> NAME/KEY: VARIANT
<222> LOCATION: (6)      (6)
<223> OTHER INFORMATION: Xaa is His or Arg.
<220> FEATURE:
<221> NAME/KEY: VARIANT
<222> LOCATION: (12) . . . (12)
<223> OTHER INFORMATION: Xaa is any amino acid.
<220> FEATURE:
<221> NAME/KEY: VARIANT
<222> LOCATION: (13) . . . (13)
<223> OTHER INFORMATION: Xaa is Lys or Arg.
<220> FEATURE:
<221> NAME/KEY: VARIANT
<222> LOCATION: (15) . . . (15)
<223> OTHER INFORMATION: Xaa is any amino acid.

<400> SEQUENCE: 9

Cys His Pro Xaa Xaa Xaa Lys Val Pro Phe Phe Xaa Xaa Arg Xaa His
 1               5                  10                  15

His Thr Cys Pro Cys Leu Pro
             20
```